US011361368B2

(12) United States Patent
Bramson et al.

(10) Patent No.: US 11,361,368 B2
(45) Date of Patent: Jun. 14, 2022

(54) METHODS FOR PET WELLNESS PLATFORM

(71) Applicant: HABI, INC., Telluride, CO (US)

(72) Inventors: Carol E. Bramson, Dover, MA (US); Marney Prince, Telluride, CO (US); Charles H. Cella, Pembroke, MA (US); Elizabeth Ann Boh, Cincinnati, OH (US); Olivier Jean Claude Fischer, Madeira, OH (US)

(73) Assignee: HABI, INC., Hingham, MA (US)

( * ) Notice: Subject to any disclaimer, the term of this patent is extended or adjusted under 35 U.S.C. 154(b) by 0 days.

(21) Appl. No.: 16/962,386

(22) PCT Filed: Jan. 16, 2019

(86) PCT No.: PCT/US2019/013838
§ 371 (c)(1),
(2) Date: Jul. 15, 2020

(87) PCT Pub. No.: WO2019/143714
PCT Pub. Date: Jul. 25, 2019

(65) Prior Publication Data
US 2021/0065277 A1  Mar. 4, 2021

Related U.S. Application Data

(60) Provisional application No. 62/683,925, filed on Jun. 12, 2018, provisional application No. 62/617,694, filed on Jan. 16, 2018.

(51) Int. Cl.
*G06Q 30/00* (2012.01)
*G06Q 30/06* (2012.01)
(Continued)

(52) U.S. Cl.
CPC ........ *G06Q 30/0631* (2013.01); *A01K 11/006* (2013.01); *A01K 29/005* (2013.01);
(Continued)

(58) Field of Classification Search
CPC .... G06Q 30/0601–0645; A01K 11/006; A01K 29/005; G06K 9/00362; G06K 9/6267
See application file for complete search history.

(56) References Cited

U.S. PATENT DOCUMENTS 10,721,912 B2 * 7/2020 Hanson ................. A01K 15/02
2003/0127057 A1   7/2003 Singh et al.
(Continued)

FOREIGN PATENT DOCUMENTS

KR   101721053 B1   3/2017
WO   2009079511 A1   6/2009

OTHER PUBLICATIONS

Clemons-Chevis, Connie. "Help Your Dog Resolve Emotional Issues." Tribune—Review / Pittsburgh Tribune—Review, Sep. 15, 2009, p. n/a. ProQuest. Web. Jul. 6, 2021 . (Year: 2009).*
(Continued)

*Primary Examiner* — Jeffrey A. Smith
*Assistant Examiner* — Kennedy Gibson-Wynn
(74) *Attorney, Agent, or Firm* — RMCK Law Group, PLC

(57) ABSTRACT

According to some embodiments of the present disclosure, a method for recommending pet food for a pet is disclosed. The method includes receiving pet information corresponding to the pet from a client user device of a user associated with the pet and generating a set of attributes relating to the pet based on the pet information. The method further includes determining a temperature classification corresponding to the pet based on the set of attributes and determining a recipe score corresponding to the pet based
(Continued)

upon the temperature classification and the set of attributes. The method further includes determining a pet food recommendation from a pet product database based on the temperature classification, and providing a diet recommendation indicating the pet food recommendation the user via a communication network.

20 Claims, 7 Drawing Sheets

(51) Int. Cl.
    *A01K 11/00*     (2006.01)
    *A01K 29/00*     (2006.01)
    *G06K 9/62*     (2022.01)
    *G06V 40/10*     (2022.01)

(52) U.S. Cl.
    CPC ....... *G06K 9/6267* (2013.01); *G06Q 30/0621* (2013.01); *G06V 40/10* (2022.01)

(56) References Cited

U.S. PATENT DOCUMENTS

| | | |
|---|---|---|
| 2006/0036419 A1 | 2/2006 | Cook et al. |
| 2009/0299821 A1 | 12/2009 | Willcocks et al. |
| 2011/0274783 A1 | 11/2011 | Lee |
| 2016/0012748 A1 | 1/2016 | Donavon |
| 2016/0042038 A1 | 2/2016 | Schumacher et al. |
| 2017/0196196 A1* | 7/2017 | Trottier ................. A01K 5/0283 |
| 2018/0233223 A1* | 8/2018 | Solari ..................... G16H 20/60 |
| 2018/0322249 A1* | 11/2018 | Allen ..................... G06F 19/322 |

OTHER PUBLICATIONS

Chang, Hsiao-Chih. "Understand the Food Cure with Chinese Yin-Yang Theory." S.T.E.A.M. & Education, Boston University, 2015 (Year: 2015).*

Wu, Qunli, and Xiaochun Liang. "Food Therapy and Medical Diet Therapy of Traditional Chinese Medicine." Clinical Nutrition Experimental, vol. 18, 2018, pp. 1-5, https://www.sciencedirect.com/science/article/pii/S2352939317300829, doi:https://doi.org/10.1016/j.yclnex.2018.01.001. (Year: 2018).*

PCT International Search Report and Written Opinion dated May 8, 2019 for International Application No. PCT/US2019/013838, 15 pages.

Bittel, M., "Should You Feed Your Dog a "Hot" Protein? Or a "Cold" One?," Lucky Puppy Magazine, May 30, 2016, https://www.luckypuppymag.com/should-you-feed-your-dog-a-hot-protein-or-a-cold-one, 5 pages.

Extended European Search Report dated Sep. 2, 2021 for EP Application No. 19741435.2, 11 pages.

* cited by examiner

METHODS FOR PET WELLNESS PLATFORM

CROSS-REFERENCE TO RELATED APPLICATIONS

This application is a 371 U.S. National Stage of International Application No. PCT/US2019/013838, filed Jan. 16, 2019, which claims priority to U.S. Provisional Patent Application Ser. No. 62/617,694, filed Jan. 16, 2018, entitled System and Method for Recommending Pet Foods, and U.S. Provisional Patent Application Ser. No. 62/683,925, filed Jun. 12, 2018, entitled Methods and Systems for Automation Platform for Pet Attribute Collection and Processing. Each of the applications are hereby incorporated by reference as if fully set forth herein.

FIELD

The present disclosure relates to a pet wellness platform and methods for recommending pet products for pets based on attributes of the pets.

BACKGROUND

Most commercially available pet foods, such as pet foods sold at large retailers, meet only minimal standards for nutritional quality. In some cases, some pet foods meet the minimum standards of quality by having nutrients sprayed onto them during manufacturing in forms that are not highly bioavailable to the pet that consumes them, or that are destroyed by further processing during manufacturing. These foods may contain ingredients that have adverse effects on at least some breeds and lack ingredients that are helpful to at least some breeds.

Many common pets, such as dogs and cats, vary significantly by breed in their nutritional requirements. Also, individuals within a breed can vary significantly in their nutritional requirements. For example, within a breed factors such as age, activity level, activity type, size, weight, temperament, environment, owner attributes, and other factors may affect the nutritional requirements of a pet. A need exists for automated systems and methods for recommending pet foods that are nutritionally appropriate for the species, the breed, and/or the particular attributes of the individual pet.

An appropriate dietary recommendation may ideally be highly tuned to a number of the above-referenced attributes of an individual pet; however, as the number of attributes of a pet that are relevant to a product recommendation increases, the chances for errors in identifying the attributes also increases. For example, errors resulting from lack of data, data entry errors, incomplete data entry, lack of understanding about what data is being requested, lack of normalization, misreporting, and other factors may affect the quality of the recommendations. Some attributes like activity levels and activity type may be particularly difficult to obtain accurately because owners may only have a general (and often inaccurate) understanding of a pet's actual activities and/or owners may tend to report in a manner that reflects favorably on the owner, rather than in a manner that provides accurate information. A need exists for improved methods and systems for collecting relevant information about the attributes of pets that are relevant to dietary recommendations.

SUMMARY

According to some embodiments of the present disclosure, a method for recommending pet food for a pet is disclosed. The method includes receiving, by a processing system of a platform, pet information corresponding to the pet from a client user device of a user associated with the pet, sensor measurements from one or more wearable devices worn by the pet via an API of the platform, and video data from one or more home devices associated with an owner of the pet. The method further includes generating, by the processing system, a set of attributes relating to the pet based on the pet information, the sensor measurements, and the video data, the set of attributes including a temperature attribute indicating a body temperature of the pet. The method also includes determining, by the processing system, a temperature classification corresponding to the pet based on the set of attributes. The method also includes determining, by the processing system, a recipe score corresponding to the pet based upon the temperature classification and the set of attributes. The method also includes determining, by the processing system, a pet food recommendation from a pet product database based on the recipe score and a quantity of food to recommend for the pet based on the set of attributes. The method further includes providing, by the processing system, a diet recommendation indicating the pet food recommendation and the quantity of food to the user via a communication network.

In embodiments, determining the set of attributes includes structuring the pet information into one or more attributes. In some of these embodiments, the pet information includes one or more of an age of the pet, a breed of the pet, a size of the pet, and a weight of the pet and the set of attributes include one or more of an age attribute, a breed attribute, a size attribute, and a weight attribute.

In embodiments, determining the set of attributes includes structuring the sensor measurements into one or more attributes. In some of these embodiments, the sensor measurements include one or more of heartrate data, temperature data, and breath rate data and the set of attributes include one or more of a heartrate attribute, the temperature attribute, and a breath rate attribute.

In embodiments, determining the set of attributes includes: analyzing the video data using a computer-vision system to determine one or more classifications based on the video data; and structuring the one or more classifications into one or more respective attributes. In some of these embodiments, the one or more classifications include one or more of an eye clarity classification, a mood classification, a skin condition classification, and a muscle tone classification and the one or more attributes include one or more of an eye clarity attribute, a mood attribute, a skin condition attribute, and a muscle tone attribute.

In embodiments, the temperature classification is selected from one of a warm classification, a neutral classification, and a cool classification. In some of these embodiments, determining the recipe score includes: setting an initial recipe score based on the temperature classification; and selectively adjusting the recipe score based on the set of attributes. In some of these embodiments, the pet food recommendation includes selecting a first pet food with waffling ingredients when the recipe score is greater than an upper threshold, a second food with cooling ingredients when the recipe is less than a lower threshold, and a neutral food with neutral ingredients when the recipe is greater than the lower threshold and less than the upper threshold.

According to some embodiments of the present disclosure, a method for recommending pet food for a pet is disclosed. The method includes receiving, by a processing system of a platform, pet information corresponding to the pet from a client user device of a user associated with the pet and generating, by the processing system, a set of attributes relating to the pet based on the pet information. The method further includes determining, by the processing system, a temperature classification corresponding to the pet based on the set of attributes and determining, by the processing system, a recipe score corresponding to the pet based upon the temperature classification and the set of attributes. The method further includes determining, by the processing system, a pet food recommendation from a pet product database based on the temperature classification, and providing, by the processing system, a diet recommendation indicating the pet food recommendation the user via a communication network.

In embodiments, determining the set of attributes includes structuring the pet information into one or more attributes. In some of these embodiments, the pet information includes one or more of an age of the pet, a breed of the pet, a size of the pet, and a weight of the pet and the set of attributes include one or more of an age attribute, a breed attribute, a size attribute, and a weight attribute.

In embodiments, the method further includes receiving, by the processing system, sensor measurements from one or more wearable devices worn by the pet via an API of the platform. In some of these embodiments, determining the set of attributes includes structuring the sensor measurements into one or more attributes. In some of these embodiments, the sensor measurements include one or more of heartrate data, temperature data, and breath rate data and the set of attributes include one or more of a heartrate attribute, the temperature attribute, and a breath rate attribute.

In embodiments, the method further includes receiving, by the processing system, video data from one or more home devices associated with an owner of the pet. In some of these embodiments, determining the set of attributes includes: analyzing the video data using a computer-vision system to determine one or more classifications based on the video data; and structuring the one or more classifications into one or more respective attributes. In some of these embodiments, the one or more classifications include one or more of an eye clarity classification, a mood classification, a skin condition classification, and a muscle tone classification and the one or more attributes include one or more of an eye clarity attribute, a mood attribute, a skin condition attribute, and a muscle tone attribute.

In some embodiments, the temperature classification is selected from one of a warm classification, a neutral classification, and a cool classification. In some of these embodiments, the method further includes determining, by the processing system, a recipe score corresponding to the pet based upon the temperature classification and the set of attributes, including a temperature attribute indicating a body temperature of the pet. In some of these embodiments, determining the recipe score includes: setting an initial recipe score based on the temperature classification; and selectively adjusting the recipe score based on the set of attributes. In some of these embodiments, determining the pet food recommendation includes selecting a first pet food with warming ingredients when the recipe score is greater than an upper threshold, a second food with cooling ingredients when the recipe is less than a lower threshold, and a neutral food with neutral ingredients when the recipe is greater than the lower threshold and less than the upper threshold. In some embodiments, determining the pet recipe score includes inputting the set of attributes into a machine-learned scoring model that is trained to output recipe scores in response to respective sets of attributes.

According to some embodiments of the present disclosure, a method for recommending a pet treat for a pet is disclosed. The method includes receiving, by a processing system of a platform, pet information corresponding to the pet from a client user device of a user associated with the pet and sensor measurements from one or more wearable devices worn by the pet via an API of the platform. The method further includes generating, by the processing system, a set of attributes relating to the pet based on the pet information, the sensor measurements, and the video data, the set of attributes including a temperature attribute indicating a body temperature of the pet. The method also includes determining, by the processing system, a pet treat recommendation based on the set of attributes and providing, by the processing system, the pet treat recommendation to the user via a communication network.

In embodiments, determining the set of attributes includes structuring the pet information into one or more attributes. In some of these embodiments, the pet information includes one or more of an age of the pet, a breed of the pet, a size of the pet, and a weight of the pet and the set of attributes include one or more of an age attribute, a breed attribute, a size attribute, and a weight attribute.

In embodiments, determining the set of attributes includes structuring the sensor measurements into one or more attributes. In some of these embodiments, the sensor measurements include one or more of heartrate data, temperature data, and breath rate data and the set of attributes include one or more of a heartrate attribute, the temperature attribute, and a breath rate attribute.

In embodiments, the method further includes receiving, by the processing system, video data from one or more home devices associated with an owner of the pet. In some of these embodiments, determining the set of attributes includes: analyzing the video data using a computer-vision system to determine one or more classifications based on the video data; and structuring the one or more classifications into one or more respective attributes. In some embodiments, the one or more classifications include one or more of an eye clarity classification, a mood classification, a skin condition classification, and a muscle tone classification and the one or more attributes include one or more of an eye clarity attribute, a mood attribute, a skin condition attribute, and a muscle tone attribute.

In embodiments, determining the pet treat recommendation includes determining a temperature classification based on the set of attributes. In some of these embodiments, determining the pet treat recommendation includes determining a pet recipe score based on the temperature classification and the set of attributes. In some embodiments, determining the pet treat recommendation includes determining the pet treat from a product database based on the pet recipe scores and one or more ingredients of the pet treat.

According to some embodiments of the present disclosure, a method for recommending a pet supplement for a pet is disclosed. The method includes receiving, by a processing system of a platform, pet information corresponding to the pet from a client user device of a user associated with the pet and sensor measurements from one or more wearable devices worn by the pet via an API of the platform. The method further includes generating, by the processing system, a set of attributes relating to the pet based on the pet information, the sensor measurements, and the video data, the set of attributes including a temperature attribute indicating a body temperature of the pet. The method also includes determining, by the processing system, a pet supplement recommendation based on the set of attributes and providing, by the processing system, the pet supplement recommendation to the user via a communication network.

In embodiments, determining the set of attributes includes structuring the pet information into one or more attributes. In some of these embodiments, the pet information includes one or more of an age of the pet, a breed of the pet, a size of the pet, and a weight of the pet and the set of attributes include one or more of an age attribute, a breed attribute, a size attribute, and a weight attribute.

In embodiments, determining the set of attributes includes structuring the sensor measurements into one or more attributes. In some of these embodiments, the sensor measurements include one or more of heartrate data, temperature data, and breath rate data and the set of attributes include one or more of a heartrate attribute, the temperature attribute, and a breath rate attribute.

In embodiments, the method further includes receiving, by the processing system, video data from one or more home devices associated with an owner of the pet. In some of these embodiments, determining the set of attributes includes: analyzing the video data using a computer-vision system to determine one or more classifications based on the video data; and structuring the one or more classifications into one or more respective attributes. In some embodiments, the one or more classifications include one or more of an eye clarity classification, a mood classification, a skin condition classification, and a muscle tone classification and the one or more attributes include one or more of an eye clarity attribute, a mood attribute, a skin condition attribute, and a muscle tone attribute.

In embodiments, determining the pet supplement recommendation includes determining a temperature classification based on the set of attributes. In some of these embodiments, determining the pet supplement recommendation includes determining a pet recipe score based on the temperature classification and the set of attributes. In some embodiments, determining the pet supplement recommendation includes determining the pet supplement from a product database based on the pet recipe scores and one or more ingredients of the pet supplement.

Provided herein are improved methods and systems for collecting relevant information about attributes of pets that are relevant to dietary recommendations. In particular, provided herein are methods, systems, components, circuits, blocks, processes, software, hardware, modules, sub-systems, services, and other elements of a platform (collectively referred to herein as the "platform 100") for discovering, gathering, collecting, integrating, transforming, normalizing, processing, managing, and sharing data in connection with systems and methods for recommending pet foods.

Provided herein is a pet wellness system having an attribute generation system configured to generate a set of attributes relating to a pet, wherein the set of attributes is generated using a data set collected from at least one of a wearable device, an Internet of Things device, and a social media site that is linked to an identity of a pet and having a recommendation engine for recommending a dietary regimen for the pet based at least in part on the generated set of attributes.

In embodiments, the system further includes a computer vision system that receives image data corresponding to a pet and determines a mood classification of the pet based on the image data and a set of training data relating images to different mood classifications. In embodiments, the mood classification is further based on one or more attributes of the pet.

In embodiments, the system further includes a computer vision system that receives image data corresponding to a pet and determines a muscle tone classification of the pet based on the image data and a set of training data relating images to different muscle tone classifications. In embodiments, the muscle tone classification is further based on one or more attributes of the pet.

In embodiments, the system further includes a computer vision system that receives image data corresponding to a pet and determines a skin condition classification of the pet based on the image data and a set of training data relating images to different skin condition classifications. In embodiments, the skin condition classification is further based on one or more attributes of the pet.

In embodiments, the system further includes a computer vision system that receives image data corresponding to a pet and determines an eye clarity classification of the pet based on the image data and a set of training data relating images to different eye clarity classifications. In embodiments, the eye clarity classification is further based on one or more attributes of the pet.

In embodiments, the system further includes a machine learning system that receives wearable device data corresponding to a pet and determines a sleep state classification of the pet based on the wearable device data and a set of training data relating wearable device data to different sleep state classifications. In embodiments, the sleep state classification is further based on one or more attributes of the pet.

A more complete understanding of the disclosure will be appreciated from the description and accompanying drawings and the claims, which follow.

BRIEF DESCRIPTION OF THE DRAWINGS

The accompanying drawings, which are included to provide a better understanding of the disclosure, illustrate embodiment(s) of the disclosure and together with the description serve to explain the principle of the disclosure. In the drawings.

DETAILED DESCRIPTION

Figure 1:
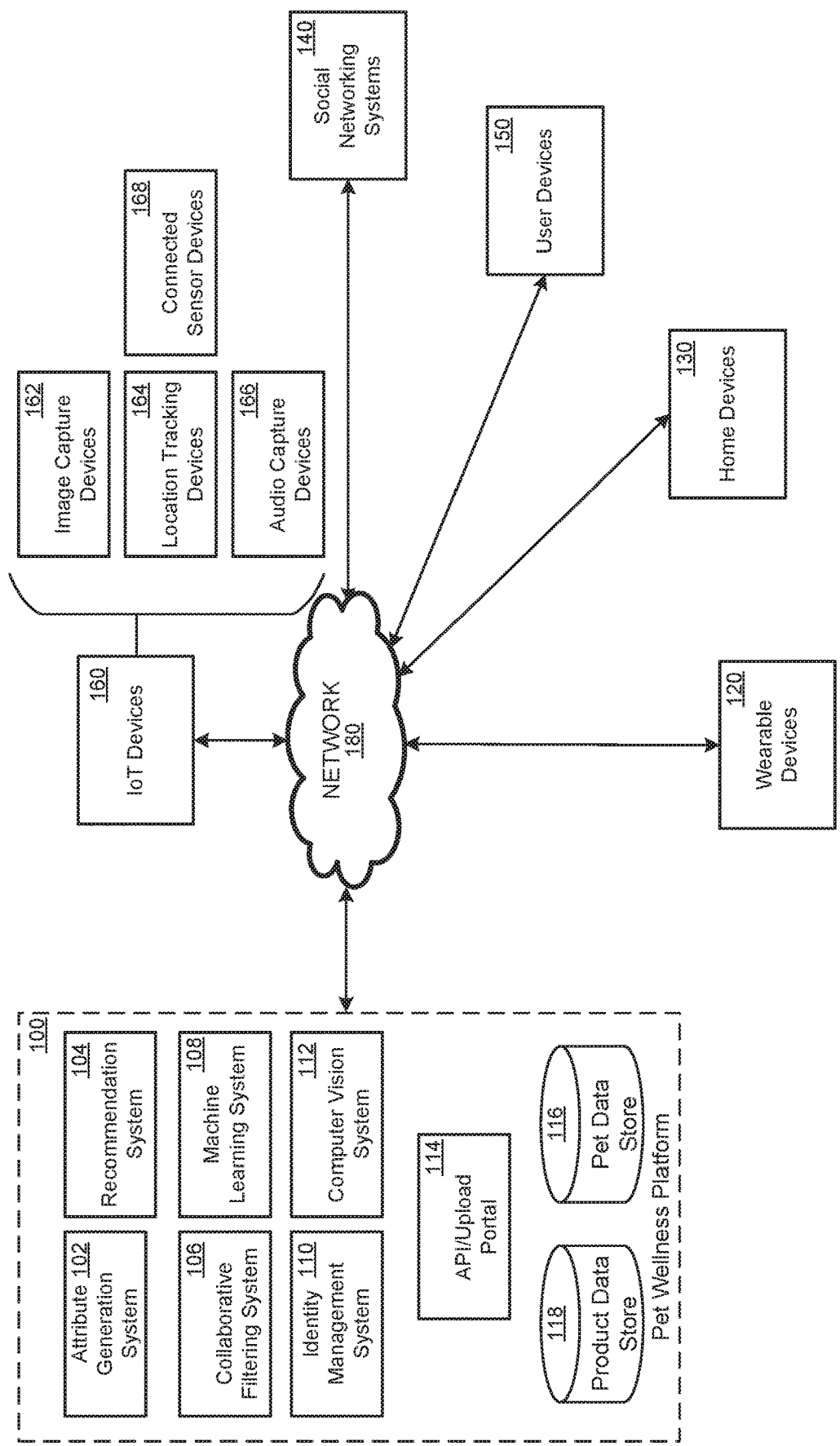
FIG. 1 depicts an example environment of a pet wellness platform according to some embodiments of the present disclosure.

FIG. 1 illustrates an example environment of a pet wellness platform 100 that collects data from wearable devices 120, Internet of Things devices 160 (e.g., image capture devices 162, tracking devices 164, audio capture devices 166, and/or connected sensor devices 168) and/or a social media system 140 that is linked to an identity of a pet. In embodiments, the pet wellness platform 100 includes an attribute generation system 102, a recommendation system 104, an identity management system 106, a machine learning system 108, a collaborative filtering system 110, a computer vision system 112, and API/Upload. Portal 114, a pet data store 116, and a product database 118. Embodiments of the pet wellness platform 100 may include additional or alternative components without departing from the scope of the disclosure.

In embodiments, the platform 100 may communicate with one or more wearable devices 120 that are worn by a pet (or owner of a pet) and that include a set of sensors that capture respective measurements relating to the pet. The set of sensors may include, for example, a motion sensor, an accelerometer, a temperature sensor, a heat flux sensor, a pressure sensor, a chemical sensor, a galvanic skin response sensor, and/or other suitable sensors. A wearable device 120 that contains a set of sensors for a pet may take many form factors, such as a band worn on or around a leg, paw, abdomen, head, neck, or the like; an adhesive patch attached to the skin (such as on the belly, the back, the inside of the ear, or the like); a collar, harness, leash element, or the like; an item of clothing (such a sweater, a sock, a hat, or the like); and many others. A wearable device 120 may be embedded in the skin of the pet, such as in the form of a microchip with embedded sensors. A wearable device 120 may include an ID device, such as an RFID device, that has identifying information encoded thereon. For example, the ID device may have a device identifier and/or pet identifier encoded thereon. In embodiments, the ID device may be a passive RFID device or an active RFID device. A wearable device 120 may include one or more elements required for location sensing, such as GPS, cellular, beacon, or other technology. In embodiments, the wearable device 120 facilitates the tracking of motion, including steps, jumps, running, side-to-side movements, acceleration, and the like. The wearable device 120 may incorporate location-tracking systems and/or processing of sensor data (e.g., integrating acceleration data from an accelerometer) to track the motion of a pet.

In embodiments, the platform 100 may be used to collect relevant images of a pet, including still images and video images. For example, an image capture device 162 may be used to capture image data (e.g., photos and/or videos) of a pet. Image data may be, for example, indicative of an activity in which the pet is engaged; the appearance of a pet (including size, weight, muscle tone, eye clarity and other wellness attributes); an owner of the pet (as well as relevant attributes of the owner, such as mood, attitude toward the pet, or the like); an energy level of the pet; performance attributes of the pet (e.g., jumping height, running speed, or agility); where the pet likes to sit or rest (e.g., as indicated by preferences for "warm" or "cold" surfaces); a mood of the pet (e.g., as indicated by posture); an environment surrounding the pet (e.g., as indicated by levels of comfort or stress), and the like. Image data may be obtained from various sources, either automatically (e.g., via an API) or by user action (e.g., via uploading, feeding, transferring; and the like). In embodiments, the platform 100 may include an API and/or upload portal 114 that receives image data (and other types of data) from a user device 150 of a pet owner, an Internet of Things device 160 (such as an access control device, security system, a baby monitor, or other device having an image capture device 162), an Internet source (such as a social media system 140), or the like.

In embodiments, the platform 100 may collect data from one or more Internet of Things (IoT) devices 160. An IoT device 160 may be any device that is capable of communicating with other devices or systems via a network (e.g., the Internet) either directly (e.g., via a WIFI connection or a cellular connection) or indirectly (e.g., through an intermediate device). IoT devices 160 may include one or more image capture devices 162, location tracking devices 164, audio capture devices 166, connected sensor devices 168, and/or any other suitable devices that are connected to a network 180. The image capture devices 162 may be any suitable devices that are capable of sensing motion, capturing images, detecting activity, and the like. A location tracking system (e.g., a beacon system, camera-based location tracking system, GPS systems, or the like) includes one or more location tracking devices 164 that are integrated with or into any device or thing that is co-present with a pet, such as a pet toy, a pet accessory, a food or water bowl, a pet carrier, a pet bed, a pet cage, a pet food dispenser, a litter box, or the like, and/or integrated with or into other household items, such as furniture, thermostats, appliances, windows, doors, desks, and the like. IoT audio capture devices 166 may include one or more devices that have audio capture capabilities, such as baby monitors, security systems, home devices, and the like.

In embodiments, the platform 100 may collect data from a social media system 140 that represents a pet and/or its owner. For example, the platform 100 may obtain image data from a social media system 140 that contains images of a pet and/or their owners. Image data may be used for various purposes noted throughout this disclosure.

In embodiments, the platform 100 may collect audio or sound data from one or more sources for use in generating recommendations and/or attributes. For example, the platform may use audio of a pet to determine stress levels (e.g., as indicated by a particular type of barking or meowing), owner interactions with a pet, and the like. Audio or sound data may come from one or more IoT devices 160 and/or user devices 150.

In embodiments, the platform 100 may collect data from a wearable device 120 worn by an owner of a pet. For example, a wearable device 120 that measures steps taken or miles covered by an owner may be linked to a device on a pet (such as an RFID tag on the collar of the pet). In some of these embodiments, the activity of the owner may be used as a proxy for the activity of the pet. The wearable device 120 of the owner may, for example, ping or read an RFID tag on the pet to confirm the proximity of the owner and the pet. Upon such confirmation, owner data may be used to infer pet data, such as miles walked during an exercise session.

Figure 2:
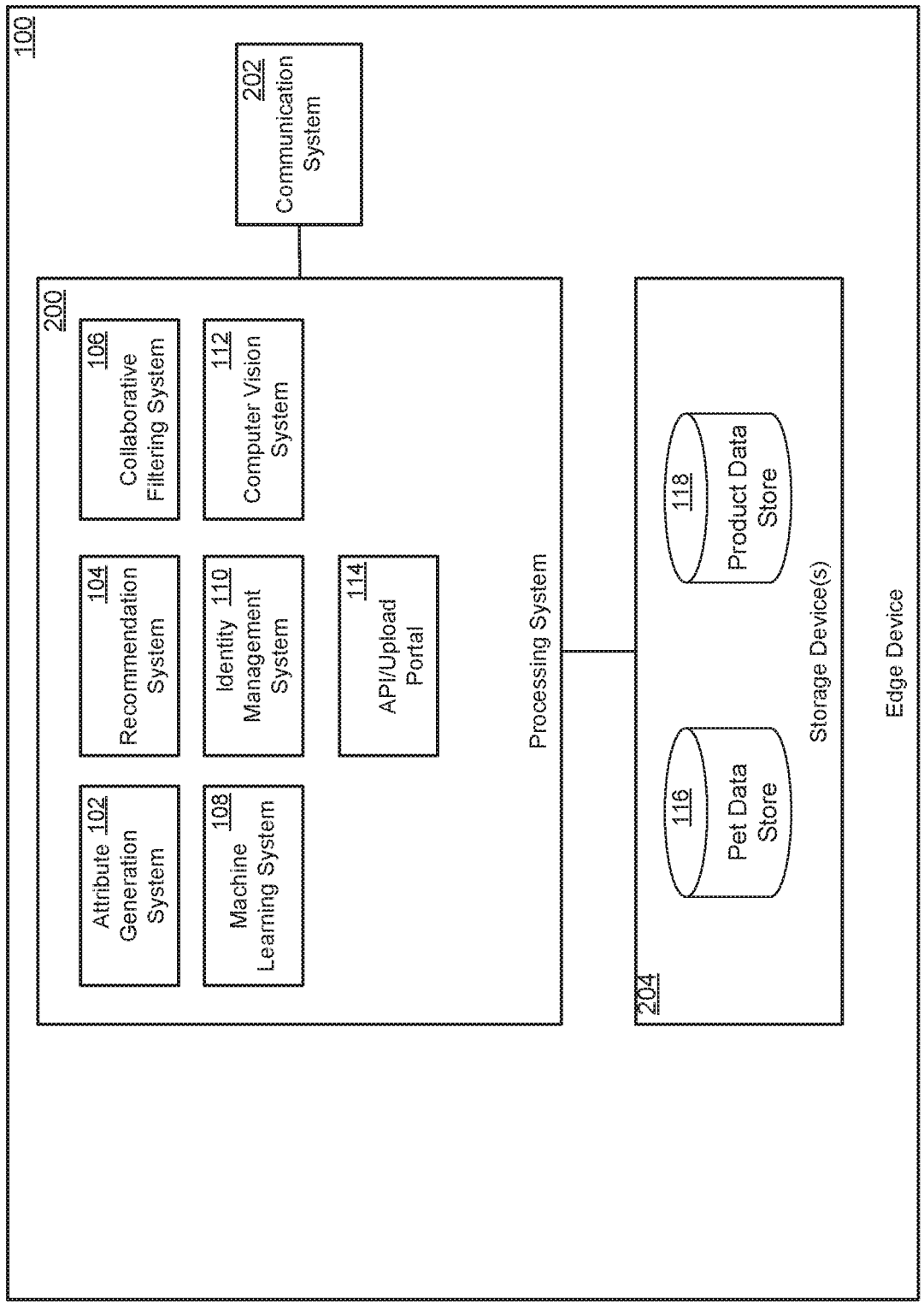
FIG. 2 depicts an example pet wellness platform according to some embodiments of the present disclosure.

FIG. 2 illustrates an example configuration of a pet wellness platform 100 according to some embodiments of the present disclosure. The platform 100 may be executed by implemented by one or more physical server devices. The platform 100 may include a processing system 200, a communication device 202, and a storage system 204.

The processing system 200 may include memory that stores computer-executable instructions and one or more processors that execute the computer-readable instructions. The processing system 200 may execute the attribute generation system 102, the recommendation system 104, the identity management system 106, the machine learning system 108, the collaborative filtering system 110, the computer vision system 112, and the API/Upload Portal 114.

The communication system 202 includes one or more communication devices, including at least one external communication device that communicates with a public communication network (e.g., the Internet). The external communication devices may perform wired or wireless communication. In embodiments, the external communication devices may include Ethernet cards, WIFI cards, and/or other suitable communication devices.

The storage system 204 includes one or more storage devices. The storage devices may include persistent storage mediums (e.g., flash memory drive, hard disk drive) and/or transient storage devices (e.g., RAM). The storage system 204 may store one or more data stores. A data store may include one or more databases, tables, indexes, records, file systems, folders and/or files. In the illustrated embodiments, the storage system 204 stores a pet data store 116 and a product data store 118. A storage system 204 may store additional or alternative data stores without departing from the scope of the disclosure.

In embodiments, the platform 100 may include a pet data store 116. In embodiments, the pet data store 116 may include a pet database that stores and indexes pet records that correspond to respective pets. Each pet record may store or be related to information of a pet. Information of a pet may include a pet identifier (e.g., a unique value that identifies the pet), an owner identifier, device identifiers (e.g., devices associated with a pet and/or an owner of the pet), a pet's name, an owner's name, a pet's breed, a pet's age, a pet's size, a pet's mood (current or average), a pet's eye clarity (current or average), a pet's muscle tone (current or average), a pet's sleep state (current or average), a pet's skin condition (current or average), a pet's diet, products bought for the pet, and the like. In some embodiments, the pet database may store a pet's medical information. In these embodiments, a pet's owner, veterinarian, or hospital may provide the pet's medical information via the API/upload portal 114. Furthermore, pet records may be grouped by one or more pet attributes. For example, pet records may be grouped by breed, age range, size, weight, activity level, diet type, and the like.

In embodiments, the pet database tracks foods consumed by a pet or group of pets, activity levels and types of a pet or group of pets, mood of a pet or group of pets, eye clarity of a pet or group of pets, muscle tone of a pet or group of pets, weight of a pet or group of pets, size of a pet or group of pets, performance of a pet or group of pets, and various other attributes over time. The data in the pet database may store and index individual data for a single pet and/or aggregated data for groups of pets (e.g., breed groups, regional groups, owner type groups, and the like). This may allow a user or operator of the platform to gather information to help identify areas that can be strengthened through food, as well as gather additional information that may be important for a user to care for a pet throughout the pet's lifetime, such as to pick up on changes that are happening in their life, such as changes in anxiety or stress, changes in environmental factors, and the like.

In embodiments, the platform 100 includes a product data store 118. In embodiments, the product data store 118 may include a product database that stores and indexes product records that correspond to respective products that may be suited for pets. Examples of products that are suited for pets include, but are not limited to, pet foods, treats, supplements, shampoos, beds, toys, exercise devices, leashes, litter boxes, crates, cages, medicines, and the like. Each product record may include a product identifier that identifies the product and product data (e.g., a product name, a product price, and/or product attributes). The platform 100 may utilize the product database, for example, when making recommendations to a user.

In embodiments, the pet identity management system 106 may link one or more devices, systems, individuals, or other items to an identity associated with an individual pet and/or an owner or caregiver for the pet. For example, an identified pet (such as having a unique identifier, such as a name, a number, or a combination) may be associated with similar identifiers for a set of one or more wearable devices 120, a set of one or more Internet of Things devices 160, a set of one or more home devices 130 (e.g., Amazon Echo® or Google Home®) a set of one or more user devices 150 of human users (e.g., owners, caregivers), other pets (e.g., other pets in a household), social media systems 140 (e.g., social media systems for the individuals associated with the pet), and the like. The identity management system 106 may be used to identify data sources that may have relevant data by which attributes about a pet may be collected and from which attributes may be interred. For example, the identity management system 106 may determine one or more devices that are associated with a particular pet from which to obtain data to be used for attribute generation and/or recommendations.

In embodiments, the attribute generation system 102 receives data from one or more data sources (e.g., a set of one or more wearable devices 120, a set of one or more Internet of Things devices 160, a set of one or more home devices 130, and/or a set one or more user devices 150) of human users (e.g., owners, caregivers) and automatically generates a set of attributes relating to a pet based thereon. The association between a data source and a particular pet may be determined by the identity management system 106. For example, the attribute generation system 102 may receive temperature data, heart rate data, and/or breath rate data from a wearable device 120 of a pet via an API of the platform 100. The attribute generation system 102 may determine a pet to which the wearable device 160 corresponds and may generate one or more attributes based on the received data. In another example, the attribute generation system 102 may receive video and/or audio data from a respective image capture device 162 and/or audio capture device 166. The attribute generation system 102 may output the video and/or audio data to the machine-learning system, which may return one or more classifications relating to the pet (e.g., temperament, activity, etc.) based on the video and/or audio data. The attribute generation system 102 may generate attributes of the pet based on the returned classifications. In embodiments, the attribute generation system 102 may add metadata to a generated attributed, such as a timestamp, date stamp, and/or a source (e.g., device ID) of the data from which the attribute was determined. The attribute generation system 102 may structure the incoming data according to a suitable schema and may store the attributes in the pet data store 116 and/or may output the attributes to the recommendation system 104.

In embodiments, the recommendation system 104 determines recommendations relating to dietary regimens or other regimens for the pet based at least in part on the generated set of attributes. In embodiments, the recommendation system 104 may determine a set of attributes relating to a pet. The attributes used to make a recommendation relating to a pet may be generated by the attribute generation system 102, may be classified by the machine learning system provided by the machine learning system 108, and/or may be provided by a user (e.g., an owner of the pet or a veterinarian of the pet). The recommendation system 104 may then determine a recommendation based on the attributes. In embodiments, the recommendation system 104 may output the attributes to the machine-learning system 108 to obtain one or more recommendations. In some of these embodiments, the machine-learning system 108 may determine recipe scores relating to different diet regimens, treat regimens, or the like, which may be used to recommend a diet regimen or treat regimen. In embodiments, the recommendation system 104 may apply one or more rules to determine or adjust a recommendation. Example methods of determining a recommendation are described in greater detail with respect to FIGS. 8 and 9.

In embodiments, the machine-learning system 108 enables and/or improves attribute determination. The machine-learning system 108 may additionally, or alternatively, improve any of the other elements of the platform 100, such as determining recommendation scores, determining classifications, or the like. In embodiments, the machine learning system 108 may be trained on outcomes, such as wellness outcomes of a pet. In embodiments, a machine learning system 108 is trained based on a set of wellness outcomes for pets that are tracked in the platform 100. In embodiments, wellness outcomes may include outcomes relating to appearance, fur/coat texture, alertness, owner perception of well-being, energy/activity levels (such as ones tracked by the platform), mood, absence of disease conditions, sleep patterns, muscle tone, eye clarity, performance (e.g., speed, agility, jumping) and other suitable types of outcomes.

In embodiments, the machine learning system 108 may implement deep learning to generate a model of attributes for a breed of pet based on tracking outcomes of activities undertaken using the platform 100. In embodiments, this may include using a convolutional neural network that is trained in a set of wellness outcomes to generate a model that associates a breed and a set of wellness outcomes with particular recommendations, such as dietary recommendations, activity recommendations, or other regimens.

In embodiments, the machine learning system 108 may train one or more machine learned models to complete a set of attributes for a pet based on a training set of data generated by a supervisor. For example, using a training data set in which a supervisor completes attribute information based on owner inputs (such as by survey) and other available data sources (such as images, such as from social media sources), a machine learning system 108 may train a model to complete other attributes that round out a profile of a pet. Such a model may provide new attributes with an estimated level of certainty, and attributes may be added to a profile for a pet that meets or exceeds a threshold level of certainty.

The machine learning system 108 may train models in any suitable manner. In embodiments, the machine-learning system 108 may implement supervised, semi-supervised, or unsupervised learning techniques. Supervised learning and semi-supervised learning may include training a machine learner using a training set created by a set of human supervisors (such where attributes are labeled by the supervisors via observation of many photographs of pets) and/or with feedback from the supervisor (such as on the success of the machine learning system in classifying attributes correctly). Embodiments may include machine learning systems 108 that are dedicated to particular attributes or combinations of attributes that can be determined by image processing, such as the type of breed of a pet, the size of the pet, the mood of the pet, activity levels and type, and many others. Embodiments of machine learning systems 108 may include neural networks, including feedforward, feedback, and convolutional neural networks, among many others. Machine learning may include model-based learning, such as where attributes (e.g., breeds of pet, ages of pets, weights of pets, and the like) are organized, such as in a hierarchy, knowledge graph, or the like, such that a machine learning system 108 may accumulate additional attributes associated with known attributes, such as learning what color patterns are associated with a given breed, or the like.

In embodiments, the platform 100 may include a collaborative filtering system 110 to identify a recommendation that is based on common attributes among pets. In embodiments, the collaborative filtering system 110 may obtain information, (e.g., by data entry, image processing, sound processing, sensor processing) that is used to generate an attribute profile for a pet and/or a pet owner. The attribute profile may be used, for example, to group pets and owners that have common attributes. In embodiments, the attribute profiles of pets and/or owners may be grouped using, for example, a similarity matrix, a clustering algorithm (such as a k-means algorithm), or the like. The collaborative filtering system 110 may use these groups to help recommend dietary regimens, activity regimens, products, and the like based on outcomes associated with other pets and/or owners in a group. Collaborative filtering, profiling, and recommendation may be improved by machine learning over time, such as using outcomes provided to or tracked by the platform 100. For example, outcomes relating to recommendations generated by the collaborative filtering system 110 may be used by the machine learning system 108 to train models that make recommendations based on one or more attributes of a pet and/or owner.

In embodiments, the platform 100 may include a computer vision system 112 that uses machine learning for automated attribute classification, such as by operating on images captured by a camera and made available to the platform (such as a mobile phone camera, access control or security camera, baby monitor, Internet of Things device or the like) and/or images obtained from a photo feed, a social network system (e.g., a social networking page of the pet owner that contains images of the pet), or the like.

Figure 3:
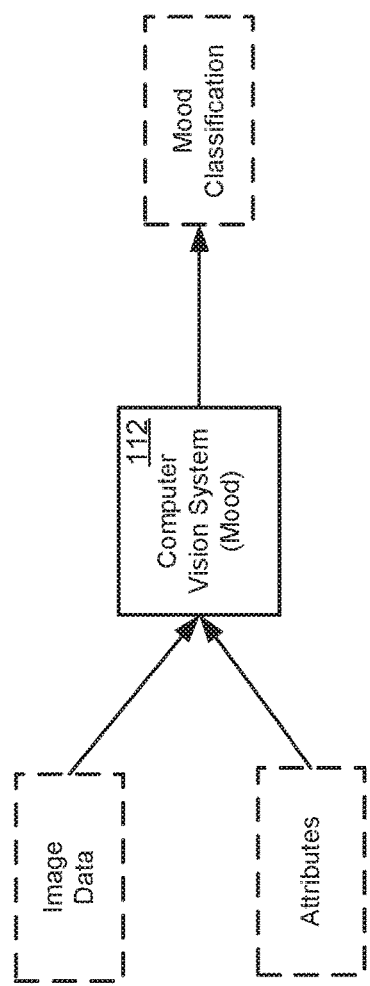
FIG. 3 depicts an example of a computer vision system configured to determine a mood classification of a pet according to some embodiments of the present disclosure.

In embodiments, the computer vision system 112 is trained to identify a mood of a pet. This may include training the computer vision system 112 on a training data set that is generated by having a set of humans indicate the mood of the pet when an image was taken, or having humans indicate the mood by simply observing a picture. The computer vision system 112 may also be trained using other attributes of pets, including an age of a pet when an image was taken, a breed of the pet, an activity level of the pet around the time an image was taken, and the like. FIG. 3 illustrates an example of a computer vision system 112 trained to identify a mood of a pet. In embodiments, the computer vision system 112 may be trained over time to classify moods from image data alone. In other embodiments, the computer vision system 112 may be trained to classify moods from image data and other attributes (e.g., age, breed, activity level). Mood classifications may be used for recommendations, which in turn may be optimized by machine learning. For example, the recommendation system 104 may be trained to provide a recommendation based on the mood of a pet and based on overall wellness outcomes that may be influenced by or associated with mood.

Figure 4:
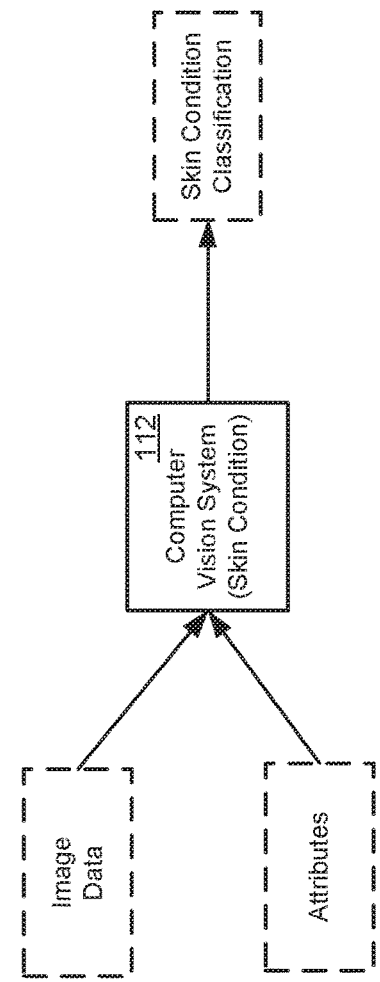
FIG. 4 depicts an example of a computer vision system configured to determine a skin condition classification of a pet according to some embodiments of the present disclosure.

In embodiments, the computer vision system 112 is trained to identify a skin condition of a pet. In these embodiments, the computer vision system 112 may be trained on a set of training data that, for example, contains images that are tagged based on the presence or absence of known conditions. FIG. 4 illustrates an example computer vision system 112 trained to identify a mood of a pet. In embodiments, the computer vision system 112 may be trained over time to classify skin conditions from image data alone. In other embodiments, the computer vision system 112 may be trained to classify skin conditions from image data and other attributes (e.g., age, breed, etc.). Skin conditions classifications may be used for recommendations, which in turn may be optimized by machine learning. For example, the recommendation system 104 may be trained to provide a recommendation to see a vet based on the skin condition of a pet and based on overall wellness outcomes that may be influenced by or associated with a skin condition.

Figure 5:
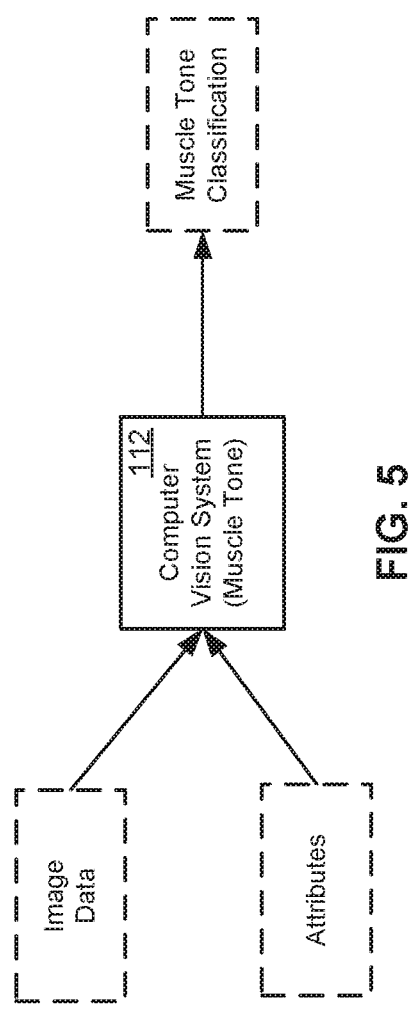
FIG. 5 depicts an example of a computer vision system configured to determine a muscle tone classification of a pet according to some embodiments of the present disclosure.

In embodiments, the computer vision system 112 is trained to identify a muscle tone state of a pet, as shown in FIG. 5. In these embodiments, the computer vision system 112 may be trained on a set of training data that, for example, contains images that are tagged based on the presence or absence of known muscle tone states. Once trained, the computer vision system 112 may output a muscle tone state attribute of a pet (e.g., tone, obese, and the like). In embodiments, the recommendation system 104 may use a muscle tone state to make a recommendation (e.g., diet recommendation, exercise recommendation, and the like).

Figure 6:
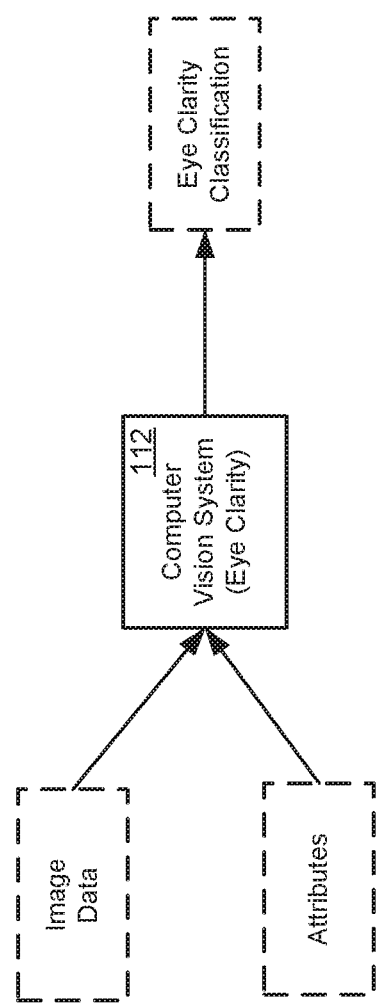
FIG. 6 depicts an example of a computer vision system configured to determine an eye clarity classification of a pet according to some embodiments of the present disclosure.

In embodiments, the computer vision system 112 is trained to identify an eye clarity state of a pet, as shown in FIG. 6. In these embodiments, the computer vision system 112 may be trained on a training set of data that includes, for example, images of pet's eyes that are tagged based on the presence or absence of known eye clarity states. Eye clarity attributes may be used by the platform 100 for example, to recommend certain diets, foods, supplements, treatments, exercises, and the like.

Figure 7:
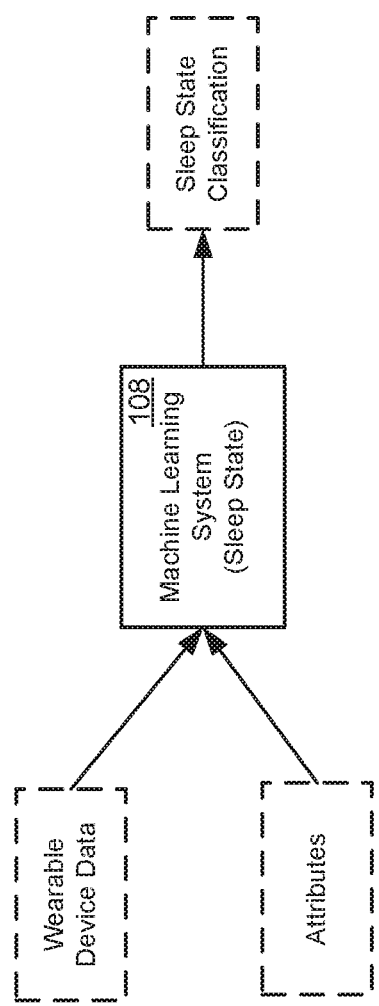
FIG. 7 depicts an example of a machine learning system configured to determine a sleep state classification of a pet according to some embodiments of the present disclosure.

In embodiments, the machine learning system 108 is trained to identify a sleep pattern of a pet based on data obtained from one or more wearable devices 120, as shown in FIG. 7. In these embodiments, the machine learning system 108 may be trained on a set of training data that, for example, includes wearable device data that is tagged based on a known sleep state of pets wearing the wearable device. Once trained, the machine learning system 108 may output a sleep attribute of a pet (e.g., a duration and/or quality of sleep), as shown in FIG. 7. A sleep attribute may be used as a wellness measure or outcome within the platform for various purposes noted herein.

In embodiments, the recommendation system 104 is configured to output breed-appropriate and/or pet-appropriate dietary recommendations based on a set of wellness outcomes for pets that are tracked in the platform. Recommendations provided in the platform may include meals, treats, pet trail mix, food toppers, broths, meal portions, sets of foods (including ones that are complementary, have desired effects, or the like), dietary regimens, portion sizes, food amounts. In these embodiments, the recommendation system 104 may provide one or more attributes (received and/or learned) to the machine-learning system 108. The machine-learning system 108 may output one or more recommended meals, treats, pet trail mix, food toppers, broths, meal portions, sets of foods (including ones that are complementary, have desired effects, or the like), dietary regimens, portion sizes, food amounts, from which the recommendation system 104 may generate a recommendation based thereon.

In embodiments, the API/upload portal 114 allows systems/users to provide pet medical information. In some embodiments, a user (e.g., an owner or person associated with a veterinary clinic) may upload electronic or scanned pet medical records. In some embodiments, a system (e.g., a pet medical record system) may upload any pet medical records specific to a pet via the API. The API/upload portal 114 may receive the pet medical records and may store the medical information contained therein in the pet record corresponding to the particular pet.

In embodiments, the platform 100 may track the activity of a pet based on the output of one or more wearable devices 120 associated with the pet or an owner of the pet. Activity tracking may include tracking steps taken by a pet, a heart rate of the pet, a jumping height of the pet, an average speed of the pet, an agility of the pet, and the like. In embodiments, observational data, such as collected by owners, may be complemented or replaced by factual data, such as collected by one or more wearable devices 120, connected sensor devices 168, the image capture device 162, or the like. In embodiments, factual data may be used to check observational data, to adjust observational data, to assist with accuracy in collection of observational data, to verify observational data, or the like. The platform 100 may store activity related data in the pet data store 116. In embodiments, the platform 100 may store and implement a set of rules regarding what data is considered the most accurate, which may be based on context or other factors. For example, observational data on activity may be used in place of data collected by a wearable device if there is an indication that the wearable device was not functioning correctly (e.g., because a battery was dead, or the like). Similarly, factual data may be used in place of observational data where factors suggest the observational data is unreliable, such as where an owner enters the exact same activity level for a pet every day for a month. Thus, data quality may be enhanced by a set of context-sensitive rules that promote the use of the best data available for a given situation.

Figure 8:
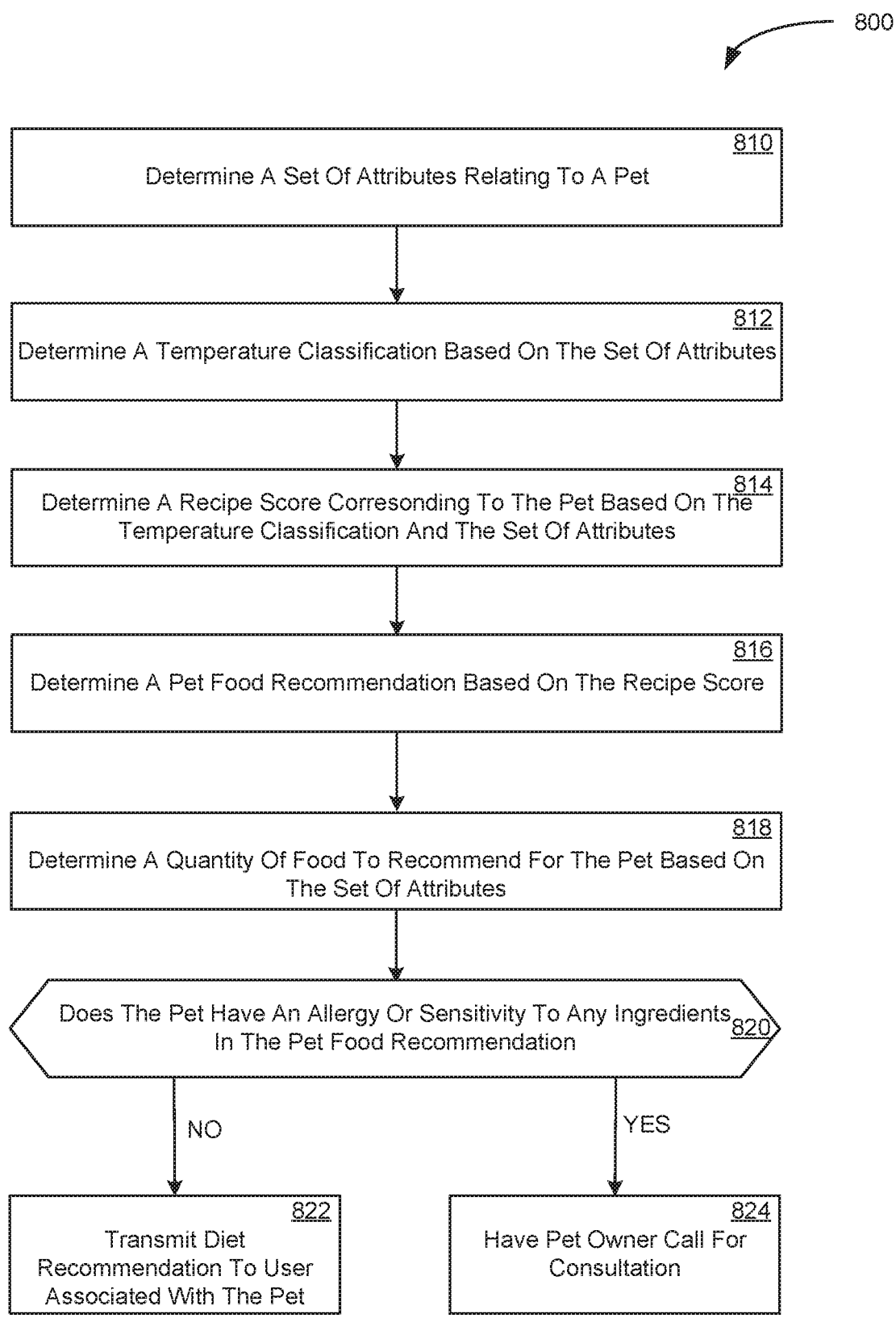
FIG. 8 depicts a flow chart illustrating a method for recommending a diet for a pet according to some embodiments of the present disclosure.
Figure 9:
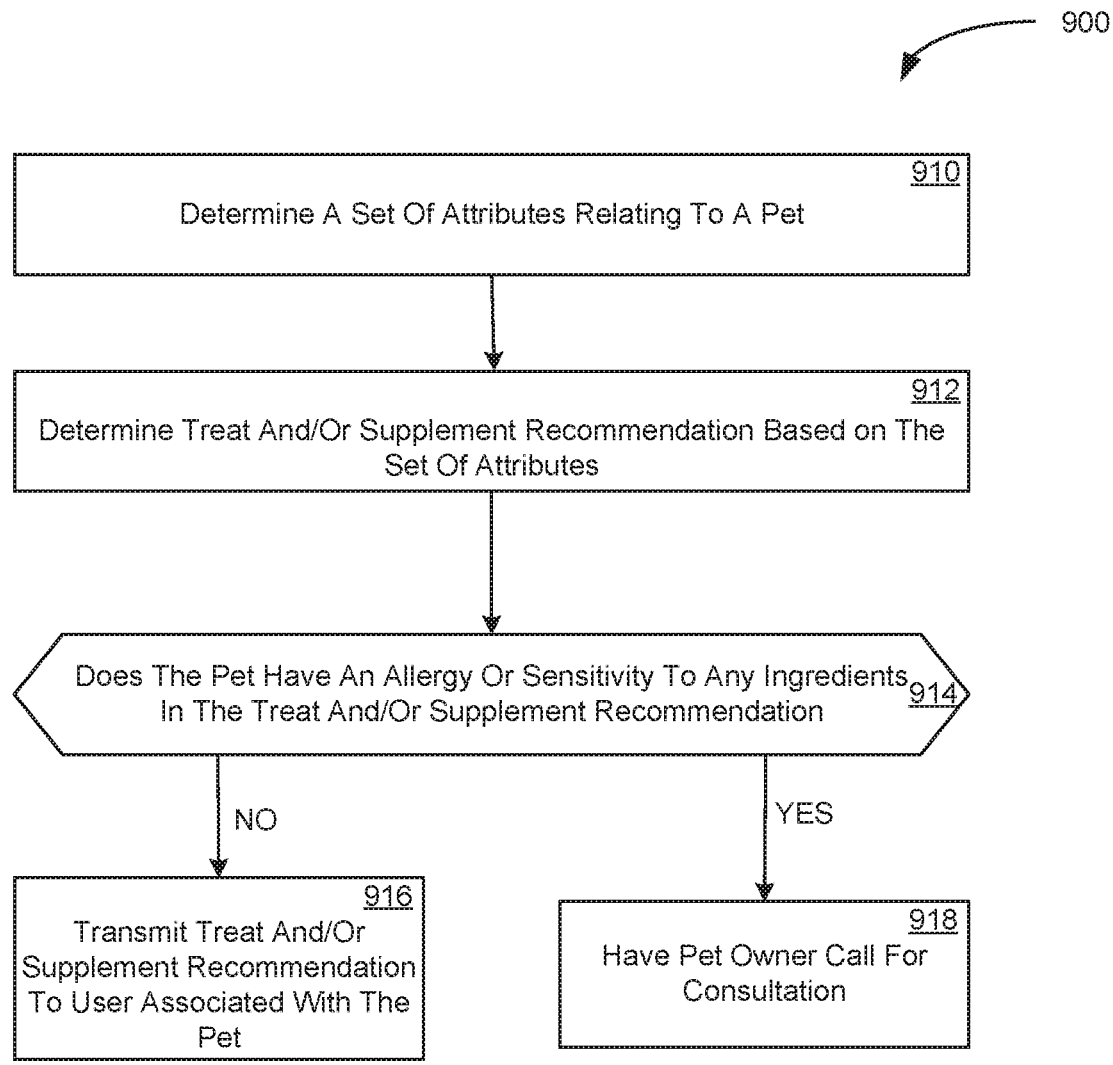
FIG. 9 depicts a flow chart illustrating a method for recommending pet treats and/or pet supplements for a pet according to some embodiments of the present disclosure.

FIGS. 8 and 9 illustrate example methods for determining recommendations for a pet. An online pet health assessment tool can approximate the manner by which veterinarians and pet nutrition specialists evaluate the pet's nutritional needs. In embodiments, the platform 100 includes a pet assessment tool that analyzes health factors, lifestyle including activities of the pet and their humans, physical and emotional environment, dietary sensitivities, and preferences, to determine the best foods, treats, supplements, and the like for a pet. Various pet input variables can be analyzed for each pet resulting in hundreds of possible combinations of unique data points. A health assessment algorithm can be used to analyze the pet information and then provide pet owners with recommended diets, treats, and supplements that correspond to the pet data to the maximum health benefit. The pet assessment tool can recommend pet food products from a single food brand or company or recommend pet food products from multiple unrelated pet food companies so that consumers can compare the ingredients from different pet food products including pet food, treats and supplements.

In embodiments, the platform 100 provides a graphical user interface with which a user can provide pet information relating to one or more pets via a user device 150. The pet information can be transmitted to the platform 100 and stored in the pet data store 116. In embodiments, the user may also link one or more wearable devices 120, home devices 130, and/or IoT devices 160 to the pet, such that the link one or more wearable devices 120, home devices 130, and/or IoT devices 160 can provide data relating to the pet to the platform 100 via an API 114. The platform 100 can process the pet information and/or any data received from various external devices 130, 140, 160 and can make a recommendation for pet food, treats and supplements for the pet.

In embodiments, the pet food recommendations can be based upon the warming or cooling characteristics of the food. Traditional Chinese medicine practitioners have used the warming and cooling nature of foods to balance the body's yin and yang to prevent and treat disease and improve the health of pets. Each ingredient of pet food can have unique cooling, warming or neutral characteristics. When cooling foods are consumed, they are adding cooling effects to a pet and eating warm foods will add warming effects to the pet. The warming and cooling foods can be used to balance the pet's body, which may be deficient in yin or yang. Chinese medicine has categorized many common foods into three thermal natures: 1) Cooling foods, 2) Warming foods and 3) Balanced, neutral foods that are neither cool nor warm. In an embodiment, the following guidelines may be implemented to determine a food's thermal properties:

1. Foods that take longer to grow, like winter squash and sweet potato, are more warming than foods that grow quickly, like celery and summer squash.
2. Blue, green, or purple foods are more cooling than similar foods that are red, orange, or yellow.
3. Tropical and subtropical foods tend to be more cooling than foods grown in temperate zones.

Table 1, provided below, provides examples of cooling foods.

TABLE 1

Cooling Foods

| Fruits | Vegetables | Grains, Legumes & Seeds | Meat, Seafood & Dairy |
|---|---|---|---|
| Tomatoes | Alfalfa sprouts | Barley | Clam |
| Apples | Asparagus | Buckwheat | Cheese |
| Banana | Bamboo shoots | Millet | Chicken |
| Kiwi | Bitter Gourd | Mung Bean | Egg |
| Mango | Broccoli | Soy Bean | Claim |
| Orange | Celery | Tofu | Crab |
| Blueberry | Chinese Radish | Wheat bran | Cream |
| Cranberry | (Daikon) | Whole wheat | Duck |
| Strawberry | Cucumber | | Egg |
| Watermelon | Eggplant | | Kelp |
| | Green leafy vegetables | | Pork |
| | Kelp | | Rabbit |
| | Lettuce | | Seaweed |
| | Lotus Root | | Turkey |
| | Mushroom | | Yogurt |
| | Spinach | | |
| | Swiss chard | | |
| | Tomato | | |
| | Water chestnut | | |
| | Watercress | | |
| | Winter Melon | | |

Cooling foods have the effect of clearing heat and toxins from the body, cooling and calming the blood and nourishing the animal. These types of food are suitable for animals that exhibit signs of excess heat in the body. Usually animals having excess heat in the body exhibit the following symptoms, including but not limited to, feeling unusually warm to the touch, excess thirst, constipation, pungent odorous wind and stools, anxiety, red eyes, swollen or shrunken tongue that is more red than usual, red/dark mucous membranes, excess dandruff, oily or dry coat ulcers in the mouth or tongue, red tongue with a thick yellow coating on the tongue, rapid pulse, heartburn and dark or yellow urine. Pets may not always be "warm" or "cool." Rather the pet may have temporary symptoms, signs or indications of an excess of heat or excess of cold that are in need of heat, etc.

A pet's activities can also indicate a need for rebalancing of cool or warm temperature for a pet. A pet that has excess heat will typically seek cool places to rest and can tend to have itchy inflamed skin. A hot pet will often be hot to the touch. A hot pet may pant excessively and may tend to itch more and act restless at bedtime. A pet that is hot may have red eyes or red skin. A hot pet may be prone to dietary sensitivities and feeding a cooling diet can be very beneficial. Hot pets can be fed cooling foods to relieve the negative effects of heat on their bodies. Proteins such as duck, rabbit, or fish are considered cooling food.

Table 2, provided below, provides examples of warming foods.

TABLE 2

Warming Foods

| Fruits | Vegetables | Grains, Legumes & Seeds | Meat, Seafood & Daily |
|---|---|---|---|
| Cherry | Ginger | Oats | Turkey |
| Peach | Turmeric | Sorghum | Chicken |
| Raspberries | Cinnamon | Sweet rice | Chicken liver |
| Blackberry | Black Strap | Quinoa | Lamb |
| Coconut | Molasses | Spelt | Pheasant |
| | Sweet Potato | | Ham |
| | Black Beans | | Mussels |
| | Squash | | Lobster |
| | Nutmeg | | Shrimp |
| | Pumpkin | | Anchovy |
| | Brussel Sprout | | Venison |
| | Kale | | Salmon |
| | Leak | | Trout |
| | Winter Squash | | Mutton |
| | | | Goat's milk |

Consumption of warming foods can have the effects of warming the body and the energy of the organs, improving the pet's circulation, and dispelling the cold. These types of food are suitable for animals that are experiencing cooling symptoms. Usually the following symptoms are associated with cooling symptoms: cold paws, cold body, shortness of breath, weakness, watery diarrhea, stomach pains or discomfort after eating or drinking cold things, bloating after eating, exercise intolerance, lack of energy, sore joints after rest and in cold weather, edema, urine or fecal incontinence, and fluid retention. Consuming warming foods can reduce or reverse these symptoms.

The pet's activities can also be associated with warm and cool tendencies. A pet that has cool tendencies should be fed warming foods. Symptoms and/or behaviors that may indicate that a pet has cool tendencies and needs a warming diet can include general weakness, fatigue, and exercise intolerance, lack of appetite and shortness of breath. These pets may act lazy and will tend to seek out warm places. Cool pets may suffer from joint stiffness and pain, especially in the winter months. These symptoms of coldness can be aided by feeding warming foods like turkey, chicken, squash, sweet potatoes and oats.

Table 3, provided below, provides examples of neutral foods.

TABLE 3

Neutral Foods

| Fruits | Vegetables | Grains, Legumes & Seeds | Meat, Seafood & Dairy |
|---|---|---|---|
| Papaya, | Beet Root | Black Soy Beans | Beef |
| Pineapple, | Cabbage, Carrots, | Kidney Beans | Goose |
| Pomegranate | Cauliflower, | Greens Beans | Salmon |
| Raspberry | Shiitake Mushroom | Peas | Tuna |
| Goji Berries | Artichoke | Red Beans | Cheese |
| Apricot | | Aduki Beans | Milk |
| Papaya | | Potato | Flaxseed |
| | | Yams | Quail |
| | | String Beans | Pork |
| | | Pumpkin | Mackerel |
| | | White Rice | Sardine |
| | | Corn | Oyster |
| | | Brown Rice | Chicken Eggs |
| | | Lentils | Cow's Milk |
| | | Sweet Potato | Honey |
| | | Rye | |
| | | Pumpkin Seed | |
| | | Sesame Seed | |
| | | Sunflower Seed | |

FIG. 8 illustrates a set of operations of a method 800 for recommending a diet for a pet. A diet for a pet may include one or more meals that are fed to a pet during the day and includes a pet food and a quantity of food to feed the pet. In embodiments, the method 800 may be executed by the platform 100.

At 810, the platform 100 determines a set of attributes relating to a pet. The platform 100 may receive input from one or more client devices (e.g., user device 150) and/or one or more other external devices (e.g., wearable devices 120, home devices 130, and/or IoT devices 160). In embodiments, pet information (e.g., breed, weight, age, etc.) corresponding to the pet may be input to a client user device 150 by a user and transmitted to the platform 100. In embodiments, the pet information may include the pet's type, breed, gender, reproductive status (e.g., intact, neutered or spayed), age, and weight. In embodiments, the user may provide additional pet information such as: activity level of the pet, body shape, pet travel, feeding habits away from home, feeding schedule, cooked or raw food preferences, dietary sensitivities, and veterinarian care. The body shape can indicate the relative weight of the pet. Examples of activity level can include: weekend warrior, which is more active on weekends, indoor pet, hiking/running/active, and lazy. Examples of body shape can include: emaciated, slim, average, overweight, and obese. The user interface can also allow users to input additional pet health information including: tongue information, eye information and temperament/personality information. The tongue information can include tongue colors such as: pale pink/almost light purple, light pink and red. The eye information can include: bright clear, yellow, yellowish whites, and discharge yellow cloudy. The pet information input by the user through the user interface can also include the pet's dietary sensitivities/allergies. The platform 100 may use the pet's dietary sensitivities/allergies to avoid any food to which the pet has dietary sensitivities or allergy. The pet information input through the user interface can include all pet dietary sensitivities known to a user.

In embodiments, the platform 100 may obtain pet-related sensor measurements from a wearable device 120 worn by the pet. Examples of pet-related sensor measurements may include, but are not limited to, temperature data, heart rate data, breath rate data, and the like. In embodiments, the platform 100 may receive image data (e.g., video data) capturing the activity of the pet from an IoT device 160.

In response to the received data, the platform 100 may determine the set of attributes relating to the pet. For example, in embodiments, the platform 100 may structure the veterinary information, temperature data, heart rate data, and/or breath rate data into attributes. Additionally or alternatively, the platform 100 may determine a classification relating to a condition of the pet based on the video data using a computer vision system 112. For example, the platform 100 may employ machine learning and/or computer vision to determine a mood classification, a skin condition classification, a sleep condition classification, a muscle tone classification, and/or an eye clarity classification based on received image data. The platform 100 may structure any determined classifications into respective attributes.

At 812, the platform 100 determines a temperature classification of the pet based on the attributes. In some embodiments, the platform 100 may determine the temperature classification based on a temperature attribute of the pet. In these embodiments, the platform 100 may utilize a lookup table or mapping that maps various temperatures or ranges of temperatures to different temperature classifications. For example, temperatures less than 101.5 degrees Fahrenheit may be associated with a cool temperature classification, temperatures between 101.5 degrees Fahrenheit and 102 degrees Fahrenheit may be associated with a neutral temperature classification, and temperatures exceeding 102 Fahrenheit may be associated with a hot temperature classification.

In other embodiments, the platform 100 may use a machine-learned classification model to determine a temperature classification of the pet. In these embodiments, the machine-learned classification model may be trained to classify a pet as being warm, neutral, or cold based on a training data set containing sets of attributes and, for each set of attributes, a classification of the pet to which the set of attributes pertains. The platform 100 may feed a set of attributes (e.g., breed, age, weight, temperature, heart rate, breath rate, mood classification, skin condition classification, sleep condition classification, muscle tone classification, and/or an eye clarity classification) to the machine-learned classification model and receives a classification indicating whether the pet is warm, neutral, or cold. Pets classified as having an excess of heat can include one or more of the following characteristics. Animals presenting with excess heat are often nervous and on edge. Pets may have a red tongue, pant excessively and seek cool floors on which to lie. Animals presenting with excess heat can have poor energy in the summer heat, show signs of excessive thirst, and present with inflamed, itchy skin, be warm to the touch, act restless at bedtime, are prone to allergies and have red eyes, skin or mucous membranes. Warm animals presenting with excess heat may also avoid warm beds, couches or carpets. In contrast to warm pets, cooling pets can display attributes that indicate that the pet is cool, calm, and collected. Cooling pets most likely will have a pale tongue, which is often wet and quite possibly engorged with teeth prints. They may prefer warm places to sleep or wish to be covered or cuddled for warmth. Animals with excess cold may suffer from exercise intolerance, lack of appetite, and/or shortness of breath. These animals generally do not like to be out in the winter and may be challenged by stiff joints during the colder months but will warm themselves in the sun or in front of warming objects (e.g., heating ducts or a fireplace). Cool animals tend to be more slow moving and sleepy and may catch colds frequently.

At 814, the platform. 100 determines a recipe score based on the temperature classification. In embodiments, a recipe score may be indicative of types and/or composition of ingredients that are to be recommended to for the pet. In embodiments, the platform 100 may determine the recipe score based on the temperature classification and the pet attributes. The platform 100 may use an algorithmic rules-based approach and/or a machine learning approach to determine the recipe score.

In embodiments, the platform 100 (e.g., the recommendation system 104) can execute a rules-based pet temperature algorithm to analyze the set of attributes relating to the pet to produce the pet recipe score. In embodiments, the pet recipe score may initially be set according to the determined temperature classification. For example, a score of 0 may be assigned to neutral animals, a score greater than 0 (e.g., 10) may be assigned to cool animals, and a score less than zero (e.g., −10) may be assigned to warns animals. In embodiments, the platform 100 may adjust the pet recipe score based on temperament factors and/or medical condition factors.

With reference to Table 4, provided below, adjustments to the pet recipe scores for temperament conditions are listed. Temperaments that are associated with warm conditions may have negative score adjustments that negatively adjust the recipe score, temperaments associated with cool conditions may have positive score adjustments that positively adjust the recipe score, and temperaments that are associated with neutral conditions can have neutral score adjustments that increase or decrease the recipe score depending if the recipe score is negative or positive (e.g., increase the recipe score when the recipe score is negative and decrease the recipe score when the score is positive).

TABLE 4

Temperaments
TEMPERAMENTS

Calm (Neutral)
Happy and Upbeat but Anxious (Neutral)
High Strung and Fearful (Warm)
High Strung and Aggressive (Warm)
Timid and Fearful (Cool)
Separation Anxiety (Cool)
Skin Is Hot to The Touch (Warm)
Panting Excessively (Warm)
Tends to Lay in Sun (Cool)
Tends to Lie in Shade (Warm)
Excessively Dry Skin (Cool)
Slow, Lazy, or Down Demeanor (Cool)

With reference to Table 5, provided below, medical conditions that may impact the recipe score are listed. Medical conditions that are associated with warm conditions may have negative score adjustments that negatively impact (e.g., decrement) the recipe score, medical conditions associated with cool conditions may have positive score adjustments that positively impact (e.g., increment) the recipe score, and neutral medical conditions can have neutral score adjustments that increase or decrease the recipe score depending if the recipe score is negative or positive (e.g., increase the recipe score when the recipe score is negative and decrease the recipe score when the score is positive).

TABLE 5

Medical Conditions
MEDICAL CONDITION

Diarrhea - thick mucus (Cool)
Diarrhea - liquid, dark, squirts (Cool)
Weight loss (Cool)
Urinary Tract Infections (Warm)
Irritated or Itchy Eyes, Eye Discharge, Eye Infection (Warm)
Scooting on his bottom (Cool)
Dental Disease (Cool)
Vomiting (Warm)
Ear Infection (Warm)
Allergic dermatitis (skin - hot spots) (Warm)
Excessive hair loss (visible spots) (Cool)
Bad Coat - Dry Skin (Cool)
Arthritis or other Joint problems (Cool)
dietary sensitivities (Cool)
Obesity (diagnosed by veteranarian) (Cool)
Diabetes
Cancer
Liver Disease
Kidney Disease
Immunodeficiency
Kennel Cough
Other disease or parasite (Heartworm, Roundworm, Lyme Disease, distemper, parvovirus, etc.)
Extreme Thirst
Recent Weight Gain or Loss of more than 05% of total body weight
None of the Above (Neutral)

In this above algorithmic approach, the platform 100 may adjust the recipe score based on each medical condition and/or temperament that is attributed to the pet to obtain the adjusted recipe score.

In a specific example of a determination of a recipe score for a pet, a pet (e.g., dog or cat) may have one or more medical conditions and one or more exhibited temperaments. For example, an analysis of an image or video of the pet may indicate that the pet exhibits irritated or itchy eyes, thick yellowish eye discharge, watery eyes, and/or an eye infection. The pet may also have allergic dermatitis, which can include skin hot spots. In this example, an adjustment value may be associated with each medical condition may be applied to a pet recipe score. For each medical condition, the platform 100 may adjust (e.g., increment or decrement) the recipe score of the pet based on the adjustment value of each respective medical condition that the pet exhibits. The platform 100 may further adjust the recipe score based on attributes relating to a pet's temperament. For example, the owner may explicitly provide pet information indicating that a pet is "high strung" or the platform 100, via analysis of a video feed of the pet, may determine that the pet's temperament is "high strung." In response to making a determination that the pet is high strung, the platform 100 may apply another adjustment value to the pet's recipe score. In this example, the cumulative adjustment to the recipe score would correspond with a negative pet recipe score, which may indicate a warm pet.

At 816, the platform 100 determines a pet food recommendation based on the recipe score. In embodiments, the platform 100 can determine whether to recommend warm, neutral or cooling pet foods based on the recipe score of the pet. Pet food ingredients have intrinsic properties that can help balance the pet's bodily energy, so pets that tend toward an overbalance of "hot" energy should consume cooling foods, while those that tend to be cold in nature should consume warming foods. A pet having a pet recipe score greater than an upper threshold (e.g., >5) can be categorized as needing warming foods. A pet having a pet recipe score below a lower threshold (e.g., <5) can be categorized as needing cooling foods. A pet having a pet recipe score between the lower and upper thresholds can be categorized as needing neutral foods.

In embodiments, the platform 100 can recommend different diets based upon distinct pet temperature recipe ranges for example: Diet A may correspond to lower pet recipe scores and may include cooling ingredients. Diets B and D may correspond to neutral pet recipe scores (e.g., between −5 to 5) and may include neutral ingredients. Diet C may correspond to higher pet recipe scores and may include warming ingredients. Table 6 illustrates a listing of diets associated with different ranges of pet recipe scores and physical conditions.

TABLE 6

Diets

| Diet | Physical Condition | Pet Recipe Score |
| --- | --- | --- |
| Diet A | Skin Allergies, hot spots, red gooey eyes, ears, inflammatory issues, UTIs, red tongue, and moves stagnations out, detoxify and clearing of liver | low pet recipe score, cooling food for a warm pet. |
| Diet B | Pets in good health, not for sick pets, geriatric, digestive problems and young pets. | Medium pet recipe score, neutral food for a neutral pet |
| Diet C | Digestive sensitivity, soothes GI tract, skin allergies. | High pet recipe score, warming food for a cool pet |
| Diet D | Pets in good health, not for immune compromised pets, geriatric, digestive problems and pets under 6 months of age. | Medium pet recipe score, neutral food for a neutral pet |

In embodiments, the platform 100 may select a pet food having warming, neutral, or cooling ingredients from the product database. In embodiments, the product database may store records that indicate different types of pet food. Each record may indicate the type of pets that the pet food is intended for (e.g., dogs or cats), sizes of the pets (e.g., large breeds, small breeds, average breeds), an age range for pets (e.g., puppy or kitten, middle-aged dog or cat, senior dog or cat), an amount of calories per serving, and the ingredients. In embodiments, the record may further indicate whether the pet food is warming, cooling, or neutral. The platform 100 may select a pet food product from the product database based on the pet recipe score, as well as other attributes of the pet, such as age, type, size, body type, and the like. For example, if a pet recipe score indicates that the pet needs warming foods, the platform. 100 may select a pet food that has warming ingredients or is designated as warming. Similarly, if the pet recipe score indicates that the pet needs cooling foods, the platform 100 may select a pet food that has cooling ingredients or is designated as cooling.

At 818, the platform determines a quantity of food to recommend for the pet based on the attributes. In embodiments, the quantity of food recommended for each pet can be at least partially based upon the breed, sex, reproductive status, weight, and/or activity level of the pet. The platform. 100 may use a lookup table or a rules-based approach to determine the quantity of food to recommend for the pet. For example, a set of pet attributes of: male neutered dog can result in the system recommending a diet of 26 calories/pound/day of food. In contrast, a set of pet attributes of male intact dog with an active lifestyle can result in the system recommending a diet of 30 calories/pound/day of food. A set of pet attributes of, female, spayed dog on a weight loss diet, the system can recommend 20 calories/pound/day of food. This daily diet can be divided between the numbers of meals that the pet eats per day. For example, if the pet is a 20-pound male neutered dog, the system can recommend 520 calories per day and if the pet eats two meals per day, the system can recommend 260 calories per meal.

At 820, the platform 100 may determine whether the recommended pet food has any ingredients to which the pet is allergic to. In embodiments, the pet record of the pet may indicate any allergies/sensitivities that the pet may have. The platform 100 may analyze the ingredients of the recommended pet food to determine whether any of the ingredients match to any of the pet's allergies or sensitivities. If not, the platform 100 may transmit a diet recommendation to the user, as shown at 822. For example, the platform 100 may generate a .json file containing the diet recommendation, links to purchase the pet food, media content (e.g., photographs or images) of the pet and/or the pet food, and may transmit the .json file to the client user device 150 of the user or to an email account of the user. The diet recommendation may include the pet food recommendation and a recommended quantity of food. The platform 100 may additionally or alternatively, store the diet recommendation in a pet record of the pet to which the diet recommendation is directed. If the recommended food contains an ingredient that the pet is allergic or sensitive to, the platform may provide a notification to the user to call for a consultation, as shown at 824. During the consultation, a customized pet food blend may be determined for the pet.

The method of FIG. 8 is provided for example and may include additional or alternative operations. For example, in embodiments, the platform 100 may filter out any pet foods that contain ingredients that the pet is sensitive or allergic to when determining the pet food recommendation at 816. In example embodiments, the platform 100 may use machine-learned scoring models to score each pet food to determine which pet food best matches to the needs of the pet.

In embodiments, after the platform 100 has analyzed the pet information including: general information, temperament information and medical issues, the platform 100 may generate a nutrition plan with a sample of recommended products (e.g., pet foods, treats, supplements, and the like), determine whether to recommend a follow up consult, and/or generate a lifestyle guide corresponding to the pet based on the pet attributes.

Table 7, provided below, illustrates an example of the inputs for basic pet information for a pet that may assist the platform 100 in determining one or more needs of the pet.

TABLE 7

Basic Pet Information Questions

| QUESTION | INPUT |
| --- | --- |
| Pet's Name | Name |
| Pet's Breed | Breed |
| Dog's Gender | Male or Female |
| What is your pet's age in years? | Age |
| What is your pet's weight in lbs.? | Weight |
| Pet's activity level? | Very low, Low, Medium, High, Very high |
| Intact/neutered/spayed status | Intact, neutered, or spayed |

The platform 100 may further request the user to input activity, lifestyle and health information for the pet. With reference to Table, 8 a list of example questions and inputs are illustrated.

TABLE 8

Activity, Lifestyle, And Health Questions

| QUESTION | INPUT |
|---|---|
| How active is your dog? | 1. Very active (over 1 hour of intense exercise daily) 2. Active (30-60 minutes of intense activity.) 3. Moderate (30-60 Minutes of leashed walks with a small amount of pant worthy exercise) 4. Minimal (approximately 30 minutes of leash walks daily). 5. Couch potato (indoor pup mostly with very little outdoor exercise to speak of.) |
| Which best describes your dog's body? Use the image at the right as a reference. Determine body condition score. | 1. Emaciated, 2. Slim, 3. Average, 4. Slightly Overweight, 5. Obese |
| Tell us a little about places you go with your dog. | 1. Every day is a new adventure. we are out and about together all the time. 2. Hiking/running/active with pet almost every day 3. Weekend warrior, which is busy during week and less active until our power weekend, 4. I love my once a week visits to the dog park but otherwise my walks are leashed and sort of boring. 5. Walk on sidewalks, 6. Spends a lot of time in backyard. 7 Indoor only |
| Does your dog often eat on the go, away from home? This may include traveling with the dog, when the dog is boarded, or even visiting with a friend or family member. | 1. Boarded often, 2. Often watched by a caregiver, 3. Camping, day trips or overnight trips with the dog, 4. Goes to work with a parent. |
| What is your dog's feeding schedule? | 1 time a day, 2 times/day, 3 times/day, 4 times/day, 5 times/day |
| Do you prefer cooked or raw options? | Raw, Cooked, varies by day of the week, varies by season, Homemade, Kibble, combo. The system can give the option to choose more than one preference. |
| Does your pet have dietary sensitivities or insensitivities to any of the following? Please check each item that the pet cannot eat. | Dietary Sensitivities: Chicken, Beef, Fish, Rabbit, Bison, Duck, Egg, Dairy (milk, yogurt, etc.), Green bean, Carrot, Spinach, Kale, Apple, Sweet potato, Pumpkin, Beets, Celery, Mint, Parsley, Grains (wheat, oats, couscous, rice, barley, corn.) Pork, Pollack, Salmon, Elk, Turkey, Lamb, |
| Tell us a little about your pet's Vet care. Please check all that apply. | 1. Pet visits the vet regularly (Annually when healthy), 2 Only visits vet when sick or injured, 3. Pet has all recommended vaccinations, 4. Pet uses a topical flea and tick preventative, 5. Pet uses a heartworm preventative, 6. Pet has had recent blood work |
| Does your dog have any of the health concerns? | Health Concerns Checklist |
| You can tell a lot about your dog by checking their tongue. Use the guide at the right to help you choose which best describes your dog. | Tongue Health Selector by Image: 1. Pale pink/almost light purple, 2. Light pink, 3. Bright pink, 4. Red. |
| Your dog's eyes are one more indicator of their overall health. Which of the following best describe your dog's eyes? | Eye Health Selector by Image: 1. yellow or yellowish whites of the eyes, 2. Discharge yellow or cloudy white 3. slightly hazy and watery appearance 4. sunken in and dry in appearance 5. bright alert and responsive |
| Which of the following best describe your dog's personality? | 1. Calm, 2. Happy and upbeat but not anxious, 3. High strung and fearful, 4. High strung and aggressive, 5. Timid and fearful, 6. Separation anxiety, 7. Bossy and in need of control, 8. Skin is hot to touch, 9. Pants excessively, 10. Excessively dry skin, 11. Tends to lay in sun, 12. Tends to lay in shade, and 13 Slow, lazy or "down" demeanor. |

FIG. 9 illustrates a set of operations of a method 900 for recommending pet treats and/or supplements for a pet based on a set of attributes. In an embodiment, the platform 100 can recommend pet treats and pet food supplements based upon a set of attributes derived from input by the pet owner via a user device 150 and/or from data received from one or more wearable devices 120, home devices 130, and/or IoT devices 160. The method may be executed by the platform 100 (e.g., the recommendation system 104).

At 910, the platform 100 determines a set of attributes corresponding to a pet. The platform 100 may receive input from one or more client devices (e.g., user device 150) and/or one or more other external devices (e.g., wearable devices 120, home devices 130, and/or IoT devices 160). In embodiments, pet information (e.g., breed, weight, age, etc.) corresponding to the pet can be input to a client user device 150 and transmitted to the platform 100. In embodiments, the pet information may include the pet's type, breed, gender, reproductive status (e.g., intact, neutered or spayed), age, weight, activity level of the pet, body shape, pet travel, feeding habits away from home, feeding schedule, cooked or raw food preferences, dietary sensitivities, and veterinarian care. In embodiments, the platform may obtain pet-related measurements from a wearable device 120 worn by the pet. Examples of pet-related measurements may include, but are not limited to, temperature data, heart rate data, breath rate data, and the like. In embodiments, the platform 100 may receive video data capturing the activity of the pet from an IoT device 160.

In response to the received data, the platform 100 may determine the set of attributes relating to the pet. For example, in embodiments, the platform 100 may structure the veterinary information, temperature data, heart rate data, and/or breath rate data into attributes. Additionally or alternatively, the platform 100 may determine a classification relating to a condition of the pet based on the video data using a computer vision system 112. For example, the platform 100 may determine a mood classification, a skin condition classification, a sleep condition classification, a muscle tone classification, and/or an eye clarity classification. The platform 100 may structure any determined classifications into a respective attribute.

At 912, the platform 100 may determine a treat and/or supplement recommendation for the pet based on the attributes. The platform 100 may determine a treat and/or supplement recommendation based on the attributes in any suitable manner. The platform 100 may employ machine-learning techniques and/or rules-based approaches.

In embodiments, the platform 100 may determine a recipe score corresponding to the pet based on the attributes of the pet. In some embodiments, the platform 100 may determine the recipe score using an algorithmic rules-based approach, as discussed with respect to FIG. 8.

In embodiments, the platform 100 may determine the recipe score corresponding to the pet using a machine-learned scoring model that is trained to determine recipe scores given a set of attributes. Such scoring models may be trained using training data pairs that include a set of attributes and a recipe score corresponding to the set of attributes.

In embodiments, the platform 100 may determine one or more treats and/or one or more supplements to recommend for the pet using the recipe score. In some of these embodiments, the platform 100 may match treats and/or supplements represented in the product datastore 118 to the pet based on the recipe score and the attributes of the pet (e.g., size, breed, age, body type, etc.).

In embodiments, the platform 100 may determine treat and/or supplement recommendations without the use of a recipe score. In these embodiments, the platform 100 may determine one or more medical conditions. For each condition, the platform 100 may match the condition to a treat or supplement. Table 9, provided below, provides examples of treats that can be matched to different conditions. Table 10, provided below, provides examples of supplements that can be matched to different conditions.

At 914, the platform 100 may determine whether a recommended treat or supplement has any ingredients to which the pet is allergic to. In embodiments, the pet record of the pet may indicate any allergies/sensitivities that the pet may have. The platform 100 may analyze the ingredients of the recommended treat or supplement to determine whether any of the ingredients match to any of the pet's allergies or sensitivities. If not, the platform 100 may transmit the treat and/or supplement recommendations to the user, as shown at 916. For example, the platform 100 may generate a json file containing the treat and/or supplement recommendations, links to purchase the treats or supplements, media content (e.g., photographs or images) of the pet and/or the recommended treats or supplements. The platform 100 may transmit the .json file to the client user device 150, whereby the recommendation is displayed to the user. The platform 100 may additionally or alternatively, store the treat and/or supplement recommendation in a pet record of the pet. If a recommended treat or supplement contains an ingredient that the pet is allergic or sensitive to, the platform may provide a notification to the user to call for a consultation, as shown at 918. During the consultation, a customized pet food blend may be determined for the pet.

The method of FIG. 9 is provided for example and may include additional or alternative operations. For example, in embodiments, the platform 100 may filter out any pet foods that contain ingredients that the pet is sensitive or allergic to when determining the supplement and/or treat recommendation at 914.

TABLE 9

Treats

| Treat | Health Match | Allergy Exclusion |
|---|---|---|
| Rabbit Duck Medallions | Diarrhea, Kidney Disease, Eye Issues, Ear Infection, and/or Food Allergies. Pets with Itchy Skin | Rabbit Duck |
| Turkey Cranberry | Urinary Tract Infection- Dogs That Run Cold | Turkey |
| Duck L'orange | Diarrhea, Eye Issues, Ear Infection, Food Allergies and/or Diabetes | Duck |
| Chicken Hearts | Allergic Dermatitis (Skin Hot Spots), Excessive Hair Loss (Visible Spots), Bad Coat Dry Skin, Diabetes, Immunodeficiency and/or Kennel Cough. | Chicken |

TABLE 9-continued

Treats

| Treat | Health Match | Allergy Exclusion |
|---|---|---|
| Chicken Gizzards | Low Taurine Diabetes, Liver Disease, Immunodeficiency, Kennel Cough Diseases and/or Parasites. | Chicken |
| Chicken Trim | Dental Disease, Vomiting, and/or Obesity | Chicken |
| Yogurt Nugget | Dental Disease, and/or Vomiting Sensitive GI Tract | Milk |
| Tail Mix - Beef | Neutral, Generally Acceptable to Most Dogs | Beef |
| Tail Mix - Duck | Cools Hot Dogs, Diarrhea, Eye Irritation, Eye Discharge, Eye Infection, Ear Infection, Food Allergies and/or Diabetes | Duck |

TABLE 10

Supplements

| Supplements | Health Match | Allergy Exclusion |
|---|---|---|
| Belly Balance | Diarrhea, and/or Scooting on Bottom. General Rebalancing of Intestinal Flora- Recommended 2x Annually for Every Outdoor Dog. | |
| Butt Bar | Scooting on Bottom- History of Anal Gland Disharmony- In Need of Bulkier Stool | Grains |
| Allergy | Eye issues, Ear Infection, and/or Food Allergies, Hot Spots, Itchy Red Skin | |
| Flexibility and Joint Issues | Joint Problems- Genetic Predisposition to Compromised Joint Health with Age | Beef |
| Skin Issues | Excessive to Minimal Hair Loss (Visible Spots) and/or Bad Coat - Dry Skin- Dandruff/Flaky Skin, Cracked Foot Pads/Cracked and Splitting Nails, Dry/Cracked Nose, Excessive Shedding | Grains |

Detailed embodiments of the present disclosure are disclosed herein; however, it is to be understood that the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed stricture.

The terms "a" or "an," as used herein, are defined as one or more than one. The term "another." as used herein, is defined as at least a second or more. The terms "including" and/or "having," as used herein, are defined as comprising (i.e., open transition).

While only a few embodiments of the present disclosure have been shown and described, it will be obvious to those skilled in the art that many changes and modifications may be made thereunto without departing from the spirit and scope of the present disclosure as described in the following claims. All patent applications and patents, both foreign and domestic, and all other publications referenced herein are incorporated herein in their entireties to the full extent permitted by law.

The methods and systems described herein may be deployed in part or in whole through a machine that executes computer software, program codes, and/or instructions on a processor. The present disclosure may be implemented as a method on the machine, as a system or apparatus as part of or in relation to the machine, or as a computer program product embodied in a computer readable medium executing on one or more of the machines. In embodiments, the processor may be part of a server, cloud server, client, network infrastructure, mobile computing platform, stationary computing platform, or other computing platforms. A processor may be any kind of computational or processing device capable of executing program instructions, codes, binary instructions and the like. The processor may be or may include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor, or any machine utilizing one, may include non-transitory memory that stores methods, codes, instructions and programs as described herein and elsewhere. The processor may access a non-transitory storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, Internet server, intranet server, cloud server, and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers, social networks, and the like. Additionally, this coupling and/or connection may facilitate remote execution of program across the network. The networking of some or all of these devices may facilitate parallel processing of a program or method at one or more location without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, Internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs, or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements. The methods and systems described herein may be adapted for use with any kind of private, community, or hybrid cloud computing network or cloud computing environment, including those which involve features of software as a service (SaaS), platform as a service (PaaS), and/or infrastructure as a service (IaaS).

The methods, program codes, and instructions described herein and elsewhere may be implemented on a cellular network having multiple cells. The cellular network may either be frequency division multiple access (FDMA) network or code division multiple access (CDMA) network.

The cellular network may include mobile devices, cell sites, base stations, repeaters, antennas, towers, and the like. The cell network may be a GSM, GPRS, 3G, EVDO, mesh, or other networks types.

The methods, program codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer-to-peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g., USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or intangible items from one state to another. The methods and systems described herein may also transform data representing physical and/or intangible items from one state to another.

The elements described and depicted herein, including in flowcharts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers and the like. Furthermore, the elements depicted in the flowchart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps associated therewith, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable devices, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine-readable medium. The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instruction.

Thus, in one aspect, methods described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the disclosure has been disclosed in connection with the preferred embodiments shown and described in detail, various modifications and improvements thereon will become readily apparent to those skilled in the art. Accordingly, the spirit and scope of the present disclosure is not to be limited by the foregoing examples but is to be understood in the broadest sense allowable by law.

The use of the terms "a" and "an" and "the" and similar referents in the context of describing the disclosure (especially in the context of the following claims) is to be construed to cover both the singular and the plural unless otherwise indicated herein or clearly contradicted by context. The terms "comprising," "having," "including," and "containing" are to be construed as open-ended terms (i.e., meaning "including, but not limited to,") unless otherwise noted. Recitations of ranges of values herein are merely intended to serve as a shorthand method of referring individually to each separate value falling within the range, unless otherwise indicated herein, and each separate value is incorporated into the specification as if it were individually recited herein. All methods described herein may be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

While the foregoing written description enables one skilled in the art to make and use what is considered presently to be the best mode thereof, those skilled in the art will understand and appreciate the existence of variations, combinations, and equivalents of the specific embodiment, method, and examples herein. The disclosure should therefore not be limited by the above-described embodiment, method, and examples, but by all embodiments and methods within the scope and spirit of the disclosure.

Any element in a claim that does not explicitly state "means for" performing a specified function, or "step for" performing a specified function, is not to be interpreted as a "means" or "step" clause as specified in 35 U.S.C. § 1120. In particular, any use of "step of" in the claims is not intended to invoke the provision of 35 U.S.C. § 112(f).

Persons skilled in the art may appreciate that numerous design configurations may be possible to enjoy the functional benefits of the inventive systems. Thus, given the wide variety of configurations and arrangements of embodiments of the present disclosure the scope of the invention is reflected by the breadth of the claims below rather than narrowed by the embodiments described above.

What is claimed is:

1. A method for recommending pet food for a pet comprising:
  receiving, by a processing system of a platform, pet information corresponding to the pet from a client user device of a user associated with the pet;
  receiving, by the processing system, sensor measurements from one or more wearable devices worn by the pet via an API of the platform;
  receiving, by the processing system, video data from one or more home devices associated with an owner of the pet;
  generating, by the processing system, a set of attributes relating to the pet based on the pet information, the sensor measurements, and the video data, the set of attributes including a temperature attribute indicating a body temperature of the pet, wherein generating the set of attributes includes:
    analyzing the video data using a computer-vision system to determine one or more classifications based on the video data, and
    structuring the one or more classifications into one or more respective attributes,
    wherein the one or more classifications include one or more of an eye clarity classification, a mood classification, a skin condition classification, or a muscle tone classification and the one or more attributes include one or more of an eye clarity attribute, a mood attribute, a skin condition attribute, or a muscle tone attribute;
  determining, by the processing system, a temperature classification corresponding to the pet based on the set of attributes;
  determining, by the processing system, a recipe score corresponding to the pet based upon the temperature classification and the set of attributes;
  determining, by the processing system, a pet food recommendation from a pet product database based on the recipe score;
  determining, by the processing system, a quantity of food to recommend for the pet based on the set of attributes; and
  providing, by the processing system, a diet recommendation indicating the pet food recommendation and the quantity of food to the user via a communication network.

2. The method of claim 1, wherein determining the set of attributes includes structuring the pet information into one or more attributes.

3. The method of claim 2, wherein the pet information includes one or more of an age of the pet, a breed of the pet, a size of the pet, and a weight of the pet and the set of attributes include one or more of an age attribute, a breed attribute, a size attribute, and a weight attribute.

4. The method of claim 1, wherein determining the set of attributes includes structuring the sensor measurements into one or more attributes.

5. The method of claim 4, wherein the sensor measurements include one or more of heart rate data, temperature data, and breath rate data and the set of attributes include one or more of a heart rate attribute, the temperature attribute, and a breath rate attribute.

6. The method of claim 1, wherein the temperature classification is selected from one of a warm classification, a neutral classification, and a cool classification.

7. The method of claim 6, wherein determining the recipe score includes:
  setting an initial recipe score based on the temperature classification; and
  selectively adjusting the recipe score based on the set of attributes.

8. The method of claim 7, wherein the pet food recommendation includes selecting a first pet food with warming ingredients when the recipe score is greater than an upper threshold, a second food with cooling ingredients when the recipe is less than a lower threshold, and a neutral food with neutral ingredients when the recipe is greater than the lower threshold and less than the upper threshold.

9. A method for recommending a pet treat for a pet comprising:
  receiving, by a processing system of a platform, pet information corresponding to the pet from a client user device of a user associated with the pet;

receiving, by the processing system, sensor measurements from one or more wearable devices worn by the pet via an API of the platform;

receiving, by the processing system, video data from one or more home devices associated with an owner of the pet;

generating, by the processing system, a set of attributes relating to the pet based on the pet information, the sensor measurements, and the video data, the set of attributes including a temperature attribute indicating a body temperature of the pet, wherein generating the set of attributes includes:

analyzing the video data using a computer-vision system to determine one or more classifications based on the video data, and structuring the one or more classifications into one or more respective attributes, wherein the one or more classifications include one or more of an eye clarity classification, a mood classification, a skin condition classification, or a muscle tone classification and the one or more attributes include one or more of an eye clarity attribute, a mood attribute, a skin condition attribute, or a muscle tone attribute;

determining, by the processing system, a pet treat recommendation based on the set of attributes; and providing, by the processing system, the pet treat recommendation to the user via a communication network.

10. The method of claim 9, wherein determining the set of attributes includes structuring the pet information into one or more attributes.

11. The method of claim 9, wherein determining the set of attributes includes structuring the sensor measurements into one or more attributes.

12. The method of claim 11, wherein the sensor measurements include one or more of heart rate data, temperature data, and breath rate data and the set of attributes include one or more of a heart rate attribute, the temperature attribute, and a breath rate attribute.

13. The method of claim 9, wherein determining the pet treat recommendation includes determining a temperature classification based on the set of attributes.

14. The method of claim 13, wherein determining the pet treat recommendation includes determining a pet recipe score based on the temperature classification and the set of attributes.

15. The method of claim 14, wherein determining the pet treat recommendation includes determining the pet treat from a product database based on the pet recipe scores and one or more ingredients of the pet treat.

16. A method for recommending pet food for a pet comprising:

receiving, by a processing system of a platform, pet information corresponding to the pet from a client user device of a user associated with the pet;

receiving, by the processing system, sensor measurements from one or more wearable devices worn by the pet via an API of the platform;

receiving, by the processing system, video data from one or more home devices associated with an owner of the pet;

generating, by the processing system, a set of attributes relating to the pet based on the pet information, the sensor measurements, and the video data, the set of attributes including a temperature attribute indicating a body temperature of the pet, wherein generating the set of attributes includes:

analyzing the video data using a computer-vision system to determine one or more classifications based on the video data, and structuring the one or more classifications into one or more respective attributes;

determining, by the processing system, a temperature classification corresponding to the pet based on the set of attributes, wherein the temperature classification is selected from one of a warm classification, a neutral classification, and a cool classification;

determining, by the processing system, a recipe score corresponding to the pet based upon the temperature classification and the set of attributes, wherein determining the recipe score includes:

setting an initial recipe score based on the temperature classification, and selectively adjusting the recipe score based on the set of attributes;

determining, by the processing system, a pet food recommendation from a pet product database based on the recipe score;

determining, by the processing system, a quantity of food to recommend for the pet based on the set of attributes; and providing, by the processing system, a diet recommendation indicating the pet food recommendation and the quantity of food to the user via a communication network.

17. The method of claim 16, wherein determining the set of attributes includes structuring the pet information into one or more attributes.

18. The method of claim 17, wherein the pet information includes one or more of an age of the pet, a breed of the pet, a size of the pet, or a weight of the pet and the set of attributes include one or more of an age attribute, a breed attribute, a size attribute, or a weight attribute.

19. The method of claim 16, wherein determining the set of attributes includes structuring the sensor measurements into one or more attributes, and wherein the sensor measurements include one or more of heart rate data, temperature data, or breath rate data and the set of attributes include one or more of a heart rate attribute, the temperature attribute, or a breath rate attribute.

20. The method of claim 16, wherein the pet food recommendation includes selecting a first pet food with warming ingredients when the recipe score is greater than an upper threshold, a second food with cooling ingredients when the recipe is less than a lower threshold, or a neutral food with neutral ingredients when the recipe is greater than the lower threshold and less than the upper threshold.

* * * * *